United States Patent
Farquhar

(10) Patent No.: US 11,457,857 B2
(45) Date of Patent: *Oct. 4, 2022

(54) MULTI-CHANNEL STIMULATION THRESHOLD DETECTION ALGORITHM FOR USE WITH NEUROPHYSIOLOGY MONITORING SYSTEMS

(71) Applicant: NuVasive, Inc., San Diego, CA (US)

(72) Inventor: Allen Farquhar, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 16/438,353

(22) Filed: Jun. 11, 2019

(65) Prior Publication Data

US 2019/0290149 A1 Sep. 26, 2019

Related U.S. Application Data

(63) Continuation of application No. 14/959,850, filed on Dec. 4, 2015, now Pat. No. 10,441,183, which is a continuation of application No. 13/960,610, filed on Aug. 6, 2013, now abandoned, which is a continuation of application No. 13/533,919, filed on Jun. 26, 2012, now Pat. No. 8,500,653, which is a continuation of application No. 11/994,409, filed as application No. PCT/US2006/037013 on Sep. 22, 2006, now Pat. No. 8,206,312.

(Continued)

(51) Int. Cl.
*A61B 5/389* (2021.01)
*A61B 5/00* (2006.01)
*A61B 5/24* (2021.01)

(52) U.S. Cl.
CPC .............. *A61B 5/389* (2021.01); *A61B 5/24* (2021.01); *A61B 5/4041* (2013.01); *A61B 5/407* (2013.01)

(58) Field of Classification Search
CPC ......... A61B 5/389; A61B 5/24; A61B 5/4041; A61B 5/407; A61B 5/4893; A61B 2017/0256; A61B 2017/00026; A61N 1/0551; A61N 1/36017; A61N 1/37247; A61N 1/08; A61N 1/36

See application file for complete search history.

(56) References Cited

U.S. PATENT DOCUMENTS

| 972,983 A | 10/1910 | Arthur |
| 1,328,624 A | 1/1920 | Graham |

(Continued)

FOREIGN PATENT DOCUMENTS

| DE | 299 08 259 | 7/1999 |
| EP | 0 759 307 | 2/1997 |

(Continued)

OTHER PUBLICATIONS

"Electromyography System," International Search Report from International Application No. PCT/US00/32329, dated Apr. 27, 2001, 9 pages.

(Continued)

*Primary Examiner* — Patrick Fernandes
(74) *Attorney, Agent, or Firm* — Seager, Tufte & Wickhem, LLP

(57) ABSTRACT

The present invention relates generally to an algorithm aimed at neurophysiology monitoring, and more particularly to an algorithm capable of quickly finding stimulation thresholds over multiple channels of a neurophysiology monitoring system.

19 Claims, 11 Drawing Sheets

Related U.S. Application Data

(60) Provisional application No. 60/719,897, filed on Sep. 22, 2005.

(56) References Cited

U.S. PATENT DOCUMENTS

| | | |
|---|---|---|
| 1,548,184 A | 8/1925 | Cameron |
| 2,704,064 A | 6/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 9/1986 | Rantala |
| 4,616,660 A | 10/1986 | Johns |
| 4,633,889 A | 1/1987 | Talalla |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,125,406 A | 6/1992 | Goldstone et al. |
| 5,127,403 A | 7/1992 | Brownlee |
| 5,161,533 A | 11/1992 | Prass et al. |
| 5,196,015 A | 3/1993 | Neubardt |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,248 A | 10/1996 | Matthews |
| 5,579,781 A | 12/1996 | Cooke |
| 5,593,429 A | 1/1997 | Ruff |
| 5,599,279 A | 2/1997 | Slotman et al. |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,779,642 A | 4/1998 | Nightengale |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,785,658 A | 7/1998 | Benaron |
| 5,797,854 A | 8/1998 | Hedgecock |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,976,094 A | 11/1999 | Gozani et al. |
| 6,004,262 A | 12/1999 | Putz et al. |
| 6,011,985 A | 1/2000 | Athan et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,139,545 A | 10/2000 | Utley |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,348,058 B1 | 2/2002 | Melkent et al. |
| 6,393,325 B1 | 5/2002 | Mann et al. |
| 6,425,859 B1 | 7/2002 | Foley et al. |
| 6,425,901 B1 | 7/2002 | Zhu et al. |
| 6,451,015 B1 | 9/2002 | Rittman, III et al. |
| 6,466,817 B1 | 10/2002 | Kaula et al. |
| 6,500,128 B2 | 12/2002 | Marino |
| 6,507,755 B1 | 1/2003 | Turner et al. |
| 6,564,078 B1 | 5/2003 | Marino et al. |
| 6,579,244 B2 | 6/2003 | Goodwin |
| 6,582,441 B1 | 6/2003 | He et al. |
| 6,585,638 B1 | 7/2003 | Yamamoto |
| 6,618,626 B2 | 9/2003 | West et al. |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,819,956 B2 | 11/2004 | DiLorenzo |
| 6,847,849 B2 | 1/2005 | Mamo et al. |
| 6,849,047 B2 | 2/2005 | Goodwin |

(56) References Cited

U.S. PATENT DOCUMENTS

| | | |
|---|---|---|
| 6,855,105 B2 | 2/2005 | Jackson, III et al. |
| 6,902,569 B2 | 6/2005 | Parmer et al. |
| 6,926,728 B2 | 8/2005 | Zucherman et al. |
| 6,929,606 B2 | 8/2005 | Ritland |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,207,949 B2 | 4/2007 | Miles et al. |
| 7,216,001 B2 | 5/2007 | Hacker et al. |
| 7,258,688 B1 | 8/2007 | Shah et al. |
| 7,294,127 B2 | 11/2007 | Leung et al. |
| 7,310,546 B2 | 12/2007 | Prass |
| 7,522,953 B2 | 4/2009 | Kaula et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0078618 A1 | 4/2003 | Fey et al. |
| 2003/0105503 A1 | 6/2003 | Marino |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0075578 A1 | 4/2005 | Gharib et al. |
| 2005/0080418 A1 | 4/2005 | Simonson et al. |
| 2005/0119660 A1 | 6/2005 | Burloin |
| 2005/0182454 A1 | 8/2005 | Gharib et al. |
| 2005/0256582 A1 | 11/2005 | Feree |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0021682 A1 | 1/2007 | Gharib et al. |
| 2007/0198062 A1 | 8/2007 | Miles et al. |
| 2007/0293782 A1 | 12/2007 | Marino |
| 2008/0015612 A1 | 1/2008 | Urmey |
| 2008/0039914 A1 | 2/2008 | Cory et al. |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |

FOREIGN PATENT DOCUMENTS

| | | |
|---|---|---|
| EP | 0 972 538 | 1/2000 |
| FR | 2 795 624 | 1/2001 |
| FR | 2 796 846 | 2/2001 |
| WO | 00/38574 | 7/2000 |
| WO | 00/66217 | 11/2000 |
| WO | 00/67645 | 11/2000 |
| WO | 01/03604 | 1/2001 |
| WO | 01/37728 | 5/2001 |
| WO | 03/026482 | 4/2003 |
| WO | 03/037170 | 5/2003 |
| WO | 04/12809 | 2/2004 |
| WO | 05/013805 | 2/2005 |
| WO | 06/084193 | 8/2006 |

OTHER PUBLICATIONS

"Nerve Proximity and Status Detection System and Method," International Search Report from International Application No. PCT/US01/18606, dated Oct. 18, 2001, 6 pages.

"Relative Nerve Movement and Status Detection System and Method," International Search Report from International Application No. PCT/US01/18579, dated Jan. 15, 2002, 6 pages.

"System and Method for Determining Nerve Proximity Direction and Pathology During Surgery," International Search Report from International Application No. PCT/US02/22247, dated Mar. 27, 2003, 4 pages.

"System and Methods for Determining Nerve Direction to a Surgical Instrument," International Search Report from International Application No. PCT/US03/02056, dated Aug. 12, 2003, 5 pages.

"Systems and Methods for Performing Percutaneous Pedicle Integrity Assessments," International Search Report from International Application No. PCT/US02/35047, dated Aug. 11, 2003, 5 pages.

"Systems and Methods for Performing Surgery Procedures and Assessments," International Search Report from International Application No. PCT/US02/30617, dated Jun. 5, 2003, 4 pages.

"Systems and Methods for Performing Neurophysiologic Assessments During Spine Surgery," International Search Report from International Application No. PCT/US06/03966, dated Oct. 23, 2006, 5 pages.

"Multi-Channel Stimulation Threshold Detection Algorithm for Use in Neurophysiology Monitoring," International Search Report from International Application No. PCT/US06/37013, dated Mar. 19, 2007, 10 pages.

Lenke et al., "Triggered Electromyographic Threshold for Accuracy of Pedicle Screw Placement," *Spine*, 1995, 20(4): 1585-1591.

"Brackmann II EMG System," *Medical Electronics*, 1999, 4 pages.

"Neurovision SE Nerve Locator/Monitor", RLN Systems Inc. Operators Manual, 1999, 22 pages.

"The Brackmann II EMG Monitoring System," Medical Electronics Co. Operator's Manual Version 1.1, 1995, 50 pages.

"The Nicolet Viking IV," Nicolet Biomedical Products, 1999, 6 pages.

Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.

Bose et al., "Neurophysiologic Monitoring of Spinal Nerve Root Function During Instrumented Posterior Lumber Spine Surgery," *Spine*, 2002, 27(13):1444-1450.

Calancie et al., "Stimulus-Evoked EMG Monitoring During Transpedicular Lumbosacral Spine Instrumentation" *Spine*, 1994, 19(24): 2780-2786.

Clements et al., "Evoked and Spontaneous Electromyography to Evaluate Lumbosacral Pedicle Screw Placement," *Spine*, 1996, 21(5): 600-604.

Danesh-Clough et al., "The Use of Evoked EMG in Detecting Misplaced Thoracolumbar Pedicle Screws," *Spine*, Orthopaedic Department Dunedin Hospital, Jun. 15, 2001, 26(12): 1313-1316.

Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.

Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.

Ford et al. "Electrical Characteristics of Peripheral Nerve Stimulators Implications for Nerve Localization," *Regional Anesthesia*, 1984, 9: 73-77.

Glassman et al., "A Prospective Analysis of Intraoperative Electromyographic Monitoring of Pedicle Screw Placement With Computed Tomographic Scan Confirmation," *Spine*, 1995, 20(12): 1375-1379.

Greenblatt et al., "Needle Nerve Stimulator-Locator: Nerve Blocks with a New Instmment for Locating Nerves," *Anesthesia& Analgesia*, 1962, 41(5): 599-602.

Haig, "Point of view," *Spine*, 2002, 27(24): 2819.

Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.

Holland et al., "Higher Electrical Stimulus Intensities are Required to Activate Chronically Compressed Nerve Roots: Implications for Intraoperative Electromyographic Pedicle Screw Testing," *Spine*,

(56) References Cited

OTHER PUBLICATIONS

Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam. 1996, pp. 144-145.
Maguire et al., "Evaluation of Intrapedicular Screw Position Using Intraoperative Evoked Electromyography," *Spine*, 1995, 20(9): 1068-1074.
Martin et al. "Initiation of Erection and Semen Release by Rectal Probe Electrostimulation (RPE)," *The Journal of Urology*, The Williams & Wilkins Co., 1983, 129: 637-642.
Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.
Pither et al., "The Use of Peripheral Nerve Stimulators for Regional Anesthesia: Review of Experimental Characteristics Technique and Clinical Applications," *Regional Anesthesia*, 1985, 10:49-58.
Raj et al., "Infraclavicular Brachial Plexus Block—A New Approach" *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4):1-6.
Raj et al., "Use of the Nerve Stimulator for Peripheral Blocks," *Regional Anesthesia*, Apr.-Jun. 1980, pp. 14-21.
Raymond et al., "The Nerve Seeker: A System for Automated Nerve Localization," *Regional Anesthesia*, 1992, 17(3): 151-162.
Shafik, "Cavernous Nerve Simulation through an Extrapelvic Subpubic Approach: Role in Penile Erection," *Eur. Urol*, 1994, 26: 98-102.
Toleikis et al., "The Usefulness of Electrical Stimulation for Assessing Pedicle Screw Replacements," *Journal of Spinal Disorder*, 2000, 13(4): 283-289.
Moed et al., "Insertion of an iliosacral implant in an animal model," Journal of Bone and Joint Surgery, Nov. 1999, 81A(11): 1529-1537.
"NIM-Response, so advanced . . . yet so simple," XoMed, Inc., 1999, 12 pages.
Moed et al., "Intraoperative monitoring with stimulus-evoked electromyography during placement of iliosacral screws," The Journal of Bone and Joint Surgery, Apr. 1998, 81A(4): 10 pages.
"New data analyzer combines the functions of six instruments in one unit" News Release, Nov. 11, 1987, 3 pages.
"NuVasive's spine surgery system cleared in the US," Pharm & Medical Industry Week, Dec. 10, 2001, 1 page.
"Risk Capital Funds," *Innovation*, Mar. 6, 1990, 172: 3 pages.

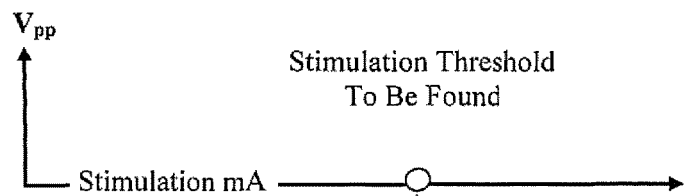
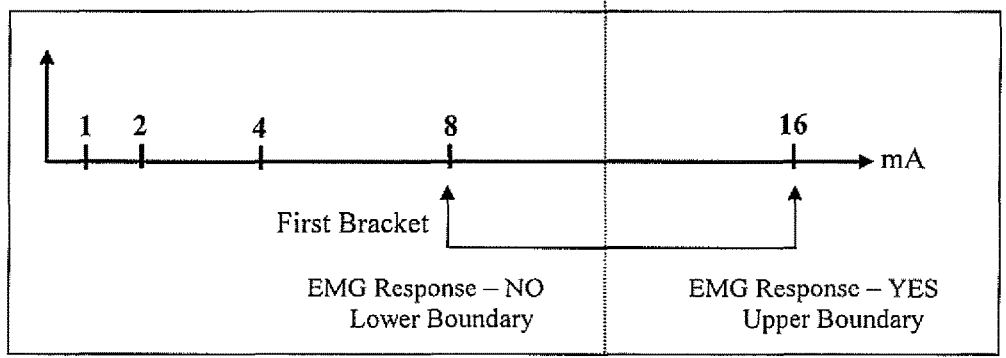
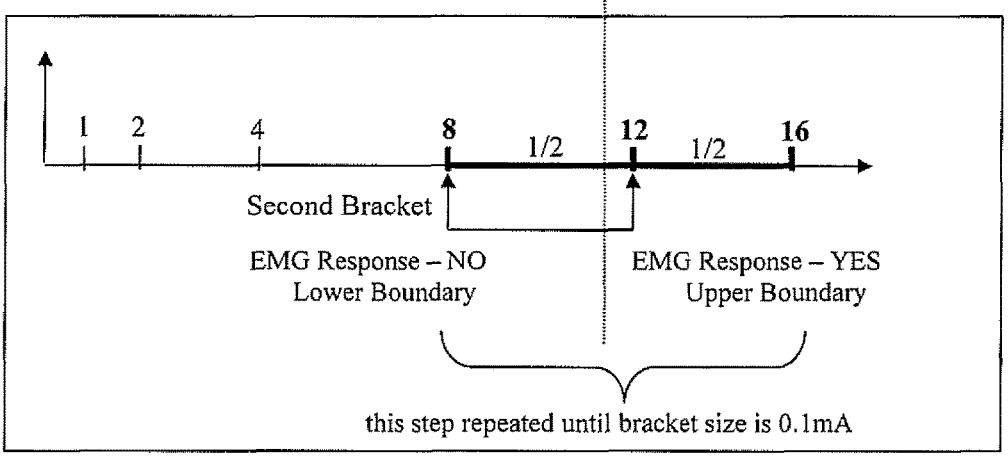
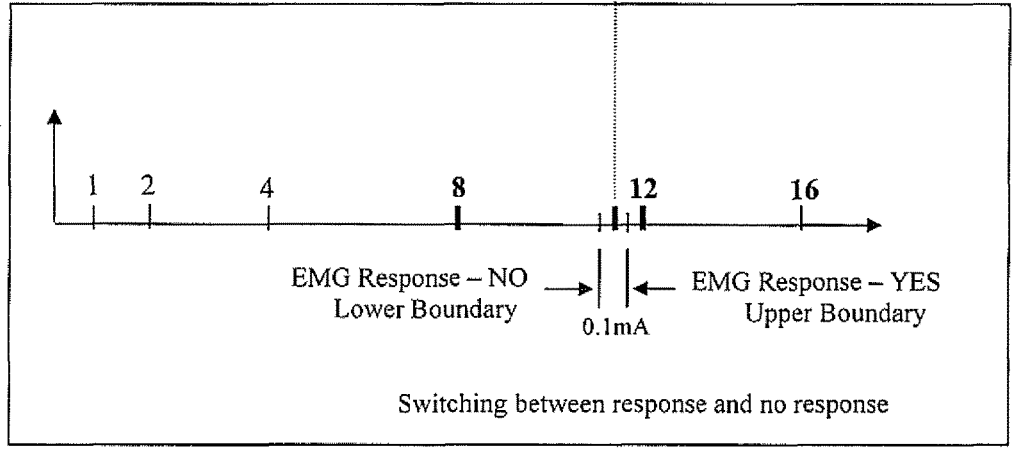

| LEGEND | |
|---|---|
| $\underline{\#}$ | = actual recruit |
| $\underline{\underline{\#}}$ | = inferred recruit |
| # | = actual nonrecruit |
| $\#$ | = inferred nonrecruit |

MULTI-CHANNEL STIMULATION THRESHOLD DETECTION ALGORITHM FOR USE WITH NEUROPHYSIOLOGY MONITORING SYSTEMS

CROSS-REFERENCE TO RELATED APPLICATIONS

This application is a continuation of U.S. patent application Ser. No. 14/959,850 filed Dec. 4, 2015, pending, which is a continuation of U.S. patent application Ser. No. 13/960,610 filed Aug. 6, 2013 (now abandoned), which is a continuation of U.S. patent application Ser. No. 13/533,919 filed Jun. 26, 2012 (now U.S. Pat. No. 8,500,653), which is a continuation of U.S. patent application Ser. No. 11/994,409 filed Dec. 31, 2007 (now U.S. Pat. No. 8,206,312), which is the national stage entry of PCT/US2006/037013 filed Sep. 22, 2006, which claims priority to U.S. Provisional Patent Application No. 60/719,897 filed Sep. 22, 2005.

BACKGROUND OF THE INVENTION

Field

The present invention relates generally to an algorithm aimed at neurophysiology monitoring, and more particularly to an algorithm capable of quickly finding stimulation thresholds over multiple channels of a neurophysiology monitoring system.

Background

The risk of neurological impairment is a prime concern when performing surgical procedures in close proximity to the spine or nerves. To combat this risk, surgeons are increasingly relying on neurophysiology monitoring techniques to monitor nerves and alert them to potential impairment during a surgical procedure. Often times effective nerve monitoring requires monitoring neurophysiologic results over a multitude of channels. While this is generally advantageous, it may have the negative effect of increasing the time required to complete nerve monitoring and therefore increasing the overall surgery time as well, which in turn increases the costs and risks associated with the surgery. Based on the foregoing, a need exists for an improved means of neurophysiology monitoring, and in particular a needs exists for a means to reduce the time required to monitor neurophysiologic results over a multitude of channels. The present invention is aimed at addressing these needs.

SUMMARY OF THE INVENTION

The present invention endows surgeons with valuable information that allows for the efficient assessment of risk to neural tissue before, during, and/or after a surgical procedure. This is accomplished by quickly and accurately determining a stimulation threshold for neural tissue and relaying that information to the surgeon in a simple comprehensible fashion. Stimulation thresholds are determined by electrically stimulating nerve tissue and analyzing resulting muscle activity relative to determine the stimulation current level at which nerve tissue depolarizes. To make stimulation threshold determinations muscle activity may be monitored by measuring electrical signals associated with muscle contraction, called electromyography ("EMG"). EMG responses can be characterized by a peak-to-peak voltage of $V_{pp}=V_{max}-V_{min}$. Characteristics of the electrical stimulation signal used may vary depending upon several factors including; the particular nerve assessment performed, the spinal target level, the type of neural tissue stimulated (e.g. nerve root, spinal cord, brain, etc. . . . ) among others.

A basic premise underlying the stimulation threshold technique is that nerves have a characteristic threshold current level ($I_{thresh}$) at which they will depolarize and cause a significant EMG response. A significant EMG response may be defined as having a $V_{pp}$ greater than a predetermined threshold voltage ($V_{thresh}$), such as, by way of example only, 100 µV. Stimulation with a current below the threshold level, $I_{thresh}$, will not evoke a significant EMG response, while stimulation with a current at or above the threshold level will evoke a significant EMG response. This relationship between the stimulation current and the EMG response may be represented via a "recruitment curve." When stimulation does not evoke a significant EMG response (represented in the onset region) the stimulation current is said to have not "recruited." When stimulation does evoke a significant EMG response (represented in the linear and saturation regions) the stimulation current is said to have "recruited." $I_{thresh}$, is the lowest stimulation current that recruits (evokes a significant EMG response).

The algorithm described herein may considerably reduce the number of stimulations, and thus time, required to determine $I_{thresh}$, particularly for a number of channels, over the course of a procedure. The basic method for finding $I_{thresh}$ utilizes a bracketing method and a bisection method. The bracketing method quickly finds a range (bracket) of stimulation currents that must contain $I_{thresh}$ and the bisection method narrows the bracket until $I_{thresh}$ is known within a specified accuracy.

The bracketing method adjusts the stimulation current as follows. Stimulation begins at a minimum stimulation current. Each subsequent stimulation is delivered at a current level double that of the preceding current. This doubling continues until a stimulation current results in an EMG response with a $V_{pp}$ greater than $V_{thresh}$. This first stimulation current to recruit, together with the last stimulation current to have not recruited, forms the initial bracket.

After bracketing the threshold current $I_{thresh}$, the bisection method is used to reduce the bracket to a selected width or resolution. The stimulation current at the midpoint of the bracket is used. If the stimulation current recruits, the bracket shrinks to the lower half of the previous range. If the stimulation current does not recruit, the bracket shrinks to the upper half of the previous range. This process continues until $I_{thresh}$ is bracketed by stimulation currents separated by the selected width or resolution. $I_{thresh}$ is preferably defined as the midpoint of this final bracket. The bracketing and bisection steps are repeated for each channel with an in range $I_{thresh}$.

To reduce the number of stimulations required to complete the bracketing and bisection steps when $I_{thresh}$ $I_{thresh}$ is determined repeatedly and/or over multiple channels, the algorithm omits stimulations for which the result is predictable from data acquired during previous stimulations. When a stimulation is omitted the algorithm proceeds as if the stimulation had taken place. However, instead of reporting an actual recruitment result, the reported result is inferred from the previous data. This permits the algorithm to proceed to the next step immediately, without the delay associated with a stimulation. For every stimulation signal delivered, the EMG response, or lack there of, is detected and recorded on each channel (no matter which channel is actually being processed for $I_{thresh}$). Later the data can be referred back to, allowing the algorithm to omit a stimulation and infer whether or not the channel would recruit at the given stimulation current.

There are two scenarios in which the algorithm may omit a stimulation and report previously obtained recruitment results. A stimulation may be omitted if the selected stimulation current would be a repeat of a previous stimulation. If the specific stimulation current is not a repeat, the stimulation may be omitted if the results are already clear from the previous data.

To determine whether to deliver an actual stimulation or omit the stimulation and report previous results, the algorithm first checks whether the selected stimulation current has been previously used. If the stimulation current has been used the stimulation is omitted and the results of the previous stimulation are reported for the present channel. If the stimulation current has not been used, the algorithm determines $I_{recruit}$ and $I_{norecruit}$ for the present channel. $I_{recruit}$ is the lowest stimulation current that has recruited on the present channel. $I_{norecruit}$ is the highest stimulation current that has failed to recruit on the present channel. If $I_{recruit}$ is not greater than $I_{norecruit}$ the algorithm will stimulate at the selected current and report the results for the present channel. If $I_{recruit}$ is greater than $I_{norecruit}$ the algorithm identifies whether the selected stimulation current is higher than $I_{recruit}$, lower than $I_{norecruit}$, or between $I_{recruit}$ and $I_{norecruit}$. If the selected stimulation current is higher than $I_{recruit}$ the algorithm omits the stimulation and reports that the present channel recruits at the specified current. Conversely, when the selected stimulation current is lower than $I_{norecruit}$ the algorithm infers that the present channel will not recruit at the selected current and reports that result. If the selected stimulation current falls between $I_{recruit}$ and $I_{norecruit}$ the result of the stimulation cannot be inferred. The algorithm stimulates at the selected current and reports the results for the present channel. This method may be repeated until $I_{thresh}$ has been determined for every active channel.

The order in which channels are processed is immaterial. The channel processing order may be biased to yield the highest or lowest threshold first or an arbitrary processing order may be used. It is also not necessary to complete the algorithm for one channel before beginning to process the next channel. Channels are still processed one at a time, however, the algorithm may cycle between one or more channels, processing as few as one stimulation current for that channel before moving on to the next channel. In this manner the algorithm may advance all channels essentially together and bias the order to find the lower threshold channels first or the higher threshold channels first.

To further reduce the number of stimulations required to repeatedly find $I_{thresh}$ over the course of a procedure, the algorithm includes a confirmation step. If $I_{thresh}$ has been previously determined for a specific channel the algorithm may simply confirm that $I_{thresh}$ has not changed rather than beginning anew with the bracketing and bisection methods. FIG. 8 illustrates the overall sequence the algorithm follows to determine $I_{thresh}$. The algorithm first determines whether it is conducting the initial threshold determination for the channel or whether there is a previous $I_{thresh}$ determination. If it is not the initial determination the algorithm confirms the previous determination. If the previous threshold is confirmed the algorithm reports that value as the present $I_{thresh}$. If it is the initial $I_{thresh}$ determination or if the previous threshold cannot be confirmed, the algorithm enters the bracketing and bisection states to determine $I_{thresh}$ and then reports the value.

The confirmation step attempts to ascertain whether $I_{thresh}$ has moved from its last known value. To do this the algorithm applies two stimulation currents, one at or just above the threshold value and one just below the threshold value. If the stimulation at or above $I_{thresh}$ recruits and the stimulation just below $I_{thresh}$ does not recruit then $I_{thresh}$ is confirmed and the algorithm may report the initial value again as $I_{thresh}$ and proceed to process another channel. If the stimulation just below $I_{thresh}$ recruits it may be concluded that $I_{thresh}$ has decreased and likewise, if the stimulation at or just above $I_{thresh}$ fails to recruit it may be assumed that $I_{thresh}$ has increased and therefore $I_{thresh}$ can not be confirmed.

If $I_{thresh}$ cannot be confirmed the algorithm enters the bracketing state. Rather than beginning the bracketing state from the minimum stimulation current, however, the bracketing state may begin from the previous $I_{thresh}$. The bracketing may advance up or down depending on whether $I_{thresh}$ has increased or decreased. When the algorithm enters the bracketing state the increment used in the confirmation step is exponentially doubled until the channel recruits, at which time it enters the bisection state. The confirmation step may be performed for each channel, in turn, in any order. Again stimulations may be omitted and the algorithm may begin processing a new channel before completing the algorithm for another channel, as described above.

The algorithm described herein may be particularly useful when employed to monitor nerve pathology in conjunction with the use of a nerve retractor. A typical nerve retractor serves to pull or otherwise maintain a nerve outside the surgical corridor, thereby protecting the nerve from inadvertent damage or contact by the "active" instrumentation used to perform the actual surgery. While generally advantageous, it has been observed that such retraction can cause nerve function to become impaired or otherwise pathologic over time due to the retraction. Monitoring $I_{thresh}$ during nerve retraction may be useful to assess the degree to which retraction of a nerve or neural structure affects the nerve function over time. One advantage of such monitoring is that the conduction of the nerve may be monitored during the procedure to determine whether the neurophysiology and/or function of the nerve changes (for the better or worse) as a result of the particular surgical procedure. For example, it may be observed that the nerve conduction decreases (indicated by an increase in $I_{thresh}$ over time) during the retraction, indicating that the nerve function has been negatively affected. In contrast, the nerve conduction may increase (indicated by a decrease in $I_{thresh}$ over time), indicating that the nerve function may have been restored or improved by the surgical procedure (such as during a successful decompression surgery, etc. . . . ). As mentioned, a change in $I_{thresh}$ may occur on any channel; therefore it is advantageous to calculate the actual $I_{thresh}$ for each channel, as opposed to determining a value for just the channel with the highest or lowest $I_{thresh}$. The algorithm of the present invention accomplishes this while substantially limiting the number of stimulations required to do so. This may substantially reduce the time required to make an $I_{thresh}$ determination which in turn may reduce the overall surgical time and risk to the patient.

The algorithm of the present invention may also be of particular use during Motor Evoked Potential (MEP) monitoring. When surgical procedures are performed in the proximity of the spinal cord, potential damage to the spinal cord is a paramount concern. Consequences of spinal cord damage may range from a slight loss of sensation to complete paralysis of the extremities, depending on the location and extent of damage. MEP monitoring, generally involving monitoring transmission of an electrical signal along the spinal cord, may be employed to assess the spinal cord before, during, and/or after surgery. Degradation or decreased conduction of an electrical signal, indicated by an increase in $I_{thresh}$, may indicate that the health of the spinal cord is compromised. Obtaining such information quickly may allow the surgeon to initiate corrective measures before the damage gets worse and/or becomes permanent. Similar to the nerve pathology monitoring mentioned above, changes in $I_{thresh}$ indicating potential damage to the spinal cord may occur on any monitored channel, thus it is advantageous to calculate the actual $I_{thresh}$ for each channel, as opposed to determining just the channel with the highest or lowest $I_{thresh}$. Employing the algorithm of the present invention again allows this to be done accurately and efficiently.

The algorithm of the present invention may be employed for use on any of a number of neurophysiology monitoring systems. By way of example only, a preferred multi-channel neurophysiology monitoring system for employing the algorithm of the present invention to quickly find stimulation thresholds for a multitude of channels may be capable of carrying out neurophysiologic assessment functions including, but not necessarily limited to, Twitch Test (neuromuscular pathway assessment), Screw Test (pedicle integrity testing), Detection (nerve proximity testing during surgical access), Nerve Retractor (nerve pathology monitoring), MEP (Motor Evoked Potential spinal cord monitoring), and SSEP (Somatosensory Evoked Potential spinal cord monitoring).

The surgical system includes a control unit, a patient module, an MEP stimulator, an EMG harness, including eight pairs of EMG electrodes and a return (anode) electrode coupled to the patient module, at least one pair of stimulation electrodes coupled to the MEP stimulator, and a host of surgical accessories (including a nerve retractor) capable of being coupled to the patient module via one or more accessory cables. Information generated by the system is shown on a screen display and may include, but is not necessarily limited to, alpha-numeric and/or graphical information regarding MEP, nerve pathology, myotome/EMG levels, stimulation levels, the function selected.

Neural pathology monitoring may be performed by electrically stimulating a nerve root according to the hunting algorithm, via one or more stimulation electrodes at the distal end of the nerve root retractor and monitoring each channel for corresponding evoked muscle responses. Threshold hunting continues according to the algorithm until $I_{thresh}$ is determined for each channel in range. A pathology assessment is made by determining a baseline stimulation threshold with direct contact between the nerve retractor and the nerve, prior to retraction. Subsequent stimulation thresholds are determined during retraction and they are compared to the baseline threshold. An increase in $I_{thresh}$ over time is an indication that the nerve function is deteriorating and retraction should be reduced or stopped altogether to prevent permanent damage. A decrease in $I_{thresh}$ over time may be an indication that nerve function has been at least partially restored. The display of $I_{thresh}$ values may be accompanied by a color code making use of the colors Red, Yellow, and Green to indicate predetermined unsafe, intermediate and safe levels, respectively.

MEP may be performed by electrically stimulating the motor cortex of the brain with electrical stimulation signals which creates an action potential that travels along the spinal cord and into the descending nerves, evoking activity from muscles innervated by the nerves. EMG responses of the muscles are recorded by the system and analyzed in relation to the stimulation signal. The multi-channel threshold hunting algorithm described above may be utilized to determine a baseline $I_{thresh}$ for each channel. Having determined a baseline $I_{thresh}$ for each channel, subsequent monitoring may be performed as desired throughout the procedure and recovery period to obtain updated $I_{thresh}$ values for each channel. Each new determination of $I_{thresh}$ is compared by the surgical system to the baseline $I_{thresh}$ for the appropriate channel. The difference ($\Delta I_{thresh}$) between the baseline $I_{thresh}$ and the new $I_{thresh}$ is calculated by the system 40 and the $\Delta I_{thresh}$ value is compared to predetermined "safe" and "unsafe" values. The display of $I_{thresh}$ may be accompanied by a color code making use of the colors Red, Yellow, and Green to indicate predetermined unsafe, intermediate and safe levels, respectively.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 5A-5D are graphs illustrating the foundation of a rapid multi-channel current threshold-hunting algorithm according to one embodiment of the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods disclosed herein boast a variety of inventive features and components that warrant patent protection, both individually and in combination.

Figure 1:
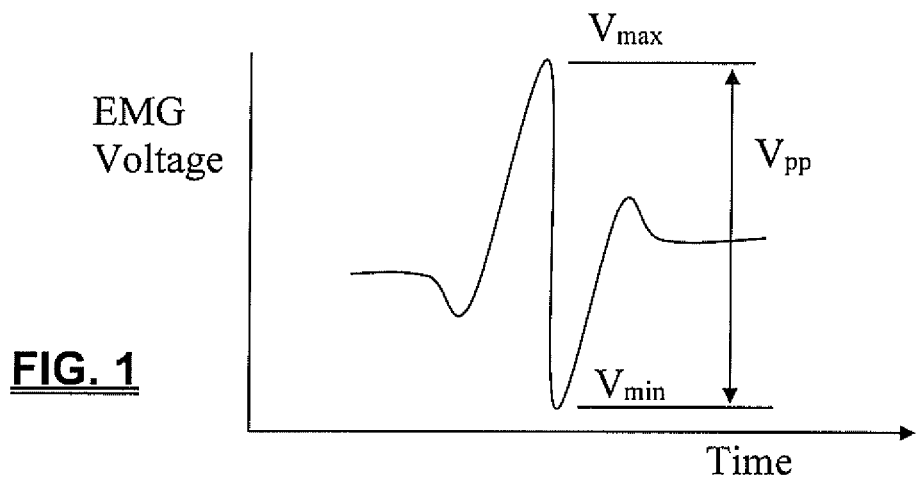
FIG. 1 is a graph illustrating a plot of the neuromuscular response (EMG) of a given myotome over time based on a current stimulation pulse applied to a nerve bundle coupled to the given myotome.
Figure 2:
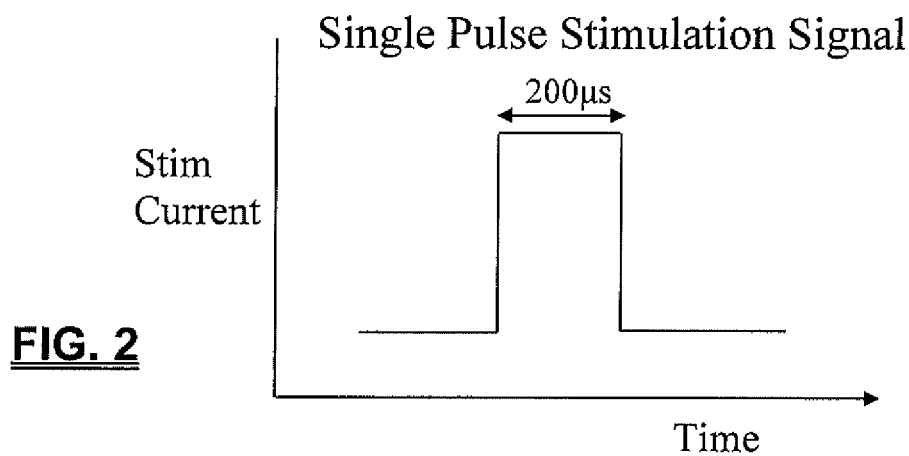
FIG. 2 is a graph illustrating a plot of a stimulation signal capable of producing a neuromuscular response (EMG) of the type shown in FIG. 1.
Figure 3:
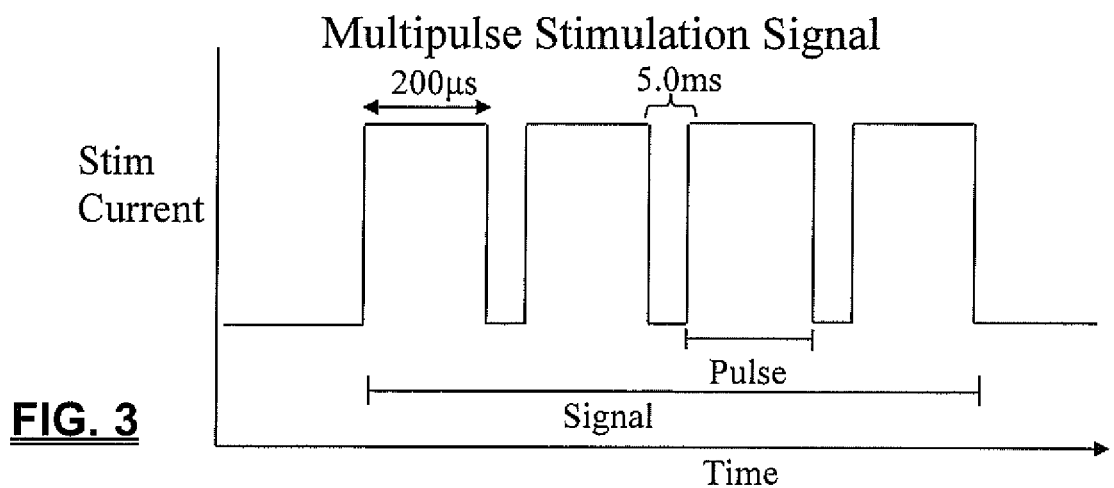
FIG. 3 is a graph illustrating a plot of another embodiment of a stimulation signal capable of producing a neuromuscular response (EMG) of the type shown in FIG. 1.

The present invention endows surgeons with valuable information that allows for the efficient assessment of risk to neural tissue before, during, and/or after a surgical procedure. This is accomplished by quickly and accurately determining a stimulation threshold for neural tissue and relaying that information to the surgeon in a simple comprehensible fashion. Stimulation thresholds are determined by electrically stimulating nerve tissue and analyzing resulting muscle activity relative to determine the stimulation current level at which nerve tissue depolarizes. To make stimulation threshold determinations muscle activity may be monitored by measuring electrical signals associated with muscle contraction, called electromyography ("EMG"). EMG responses, such as that represented in FIG. 1, can be characterized by a peak-to-peak voltage of $V_{pp}=V_{max}-V_{min}$. Characteristics of the electrical stimulation signal used may vary depending upon several factors including; the particular nerve assessment performed, the spinal target level, the type of neural tissue stimulated (e.g. nerve root, spinal cord, brain, etc. . . . ) among others. By way of example, a single pulse stimulation signal such as that illustrated by way of example in FIG. 2 or a multi-pulse stimulation signal such as that shown by way of example in FIG. 3 may be used.

Figure 4:
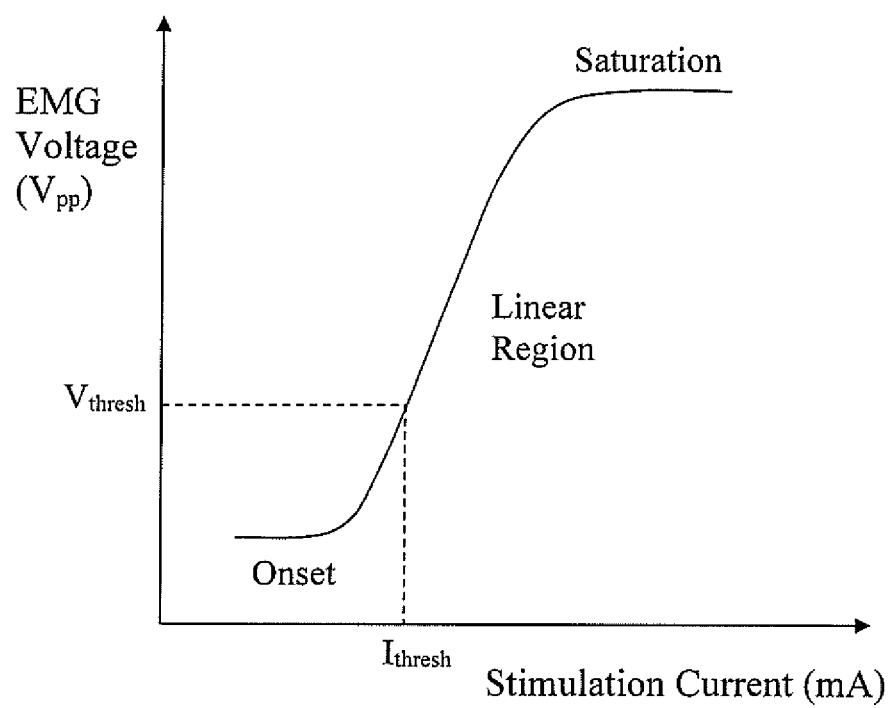
FIG. 4 is a graph illustrating a plot of peak-to-peak voltage (Vpp) for each given stimulation current level ($I_{Stim}$) forming a stimulation current pulse train according to the present invention (otherwise known as a "recruitment curve")

A basic premise underlying the stimulation threshold technique is that nerves have a characteristic threshold current level ($I_{thresh}$) at which they will depolarize and cause a significant EMG response. A significant EMG response may be defined as having a $V_{pp}$ greater than a predetermined threshold voltage ($V_{thresh}$), such as, by way of example only, 100 μN. Stimulation with a current below the threshold level, $I_{thresh}$, will not evoke a significant EMG response, while stimulation with a current at or above the threshold level will evoke a significant EMG response. This relationship between the stimulation current and the EMG response may be represented via a "recruitment curve," such as that illustrated in FIG. 4. When stimulation does not evoke a significant EMG response (represented in the onset region) the stimulation current is said to have not "recruited." When stimulation does evoke a significant EMG response (represented in the linear and saturation regions) the stimulation current is said to have "recruited." The stimulation threshold, $I_{thresh}$, is the lowest stimulation current that recruits (evokes a significant EMG response).

Knowing $I_{thresh}$ allows the surgeon to make various useful assessments regarding the safety of nerves during a surgical procedure. For example, it is often necessary to move or maintain a nerve outside of the surgical area using a nerve retractor. While retraction is generally necessary to provide better access to the surgical area and protect the nerve from inadvertent damage (e.g. through contact with various surgical implements), over time such retraction may impair nerve. A decrease in nerve function is likely to be accompanied by a corresponding increase in $I_{thresh}$ as a greater stimulation will be required to depolarize the nerve. Thus, by monitoring for changes in $I_{thresh}$ over the course of retraction, the surgeon may be alerted to potential danger and take steps to correct the condition (e.g. such as releasing or reducing pressure on the nerve) before nerve impairment gets worse and/or becomes permanent.

In many cases, to effectively utilize the valuable information $I_{thresh}$ provides, $I_{thresh}$ must be determined frequently and for a number of different channels (corresponding to different EMG recording sites and the muscles they monitor) because $I_{thresh}$ may vary between channels. Additionally, changes in $I_{thresh}$ (indicating a potential problem) may occur independently on one channel and not another, thereby necessitating repeated determinations over multiple channels in order to gain the maximum benefit. Numerous stimulations may potentially be required to make a single Ithresh determination and making $I_{thresh}$ determinations for multiple channels significantly increases this potential. For each stimulation signal emitted, a certain period of time (equaling the signal duration plus nerve recovery time) is exhausted. Over a number of stimulations this time adds up, such that the surgeon may experience a lag time upwards of 30 seconds or longer between initiating a test and receiving the $I_{thresh}$ for each channel. Added over an entire procedure this may amount to a significant increase in surgery time and/or a reluctance to monitor effectively.

The algorithm described herein may considerably reduce the number of stimulations, and thus time, required to determine $I_{thresh}$. This reduction may be especially evident when determining $I_{thresh}$ over every channel of a multi-channel neurophysiology monitoring system, such as that described below. FIGS. 5A-5D illustrate the fundamental steps of a threshold hunting algorithm used to quickly and accurately determine $I_{thresh}$. $I_{thresh}$ is, once again, the minimum stimulation current ($I_{stim}$) that results in an EMG response with a $V_{pp}$ greater than a known threshold voltage, $V_{thresh}$. The basic method for finding $I_{thresh}$ utilizes a combination of a bracketing method and a bisection method. The bracketing method quickly finds a range (bracket) of stimulation currents that must contain $I_{thresh}$ and the bisection method narrows the bracket until $I_{thresh}$ is known within a specified accuracy. If $I_{thresh}$ on a given channel exceeds a predetermined maximum stimulation current, that threshold is considered out of range.

To find the initial bracket the bracketing method adjusts the stimulation current as follows. Stimulation begins at a predetermined minimum stimulation current. The minimum stimulation current depends upon the selected function, by way of example only, the minimum stimulation current used for nerve pathology monitoring may be 0.2 mA while the minimum stimulation current used for MEP monitoring may be 60 mA. Each subsequent stimulation is delivered at a current level double that of the preceding current. This exponential doubling continues until a stimulation current results in an EMG response with a $V_{pp}$ greater than $V_{thresh}$ (i.e. it recruits). This first stimulation current to recruit, together with the last stimulation current to have not recruited, forms the initial bracket, as illustrated in FIG. 5B.

With respect to FIGS. 5C and 5D, after bracketing $I_{thresh}$, the bisection method is used as follows to reduce the bracket to a selected width, shown here by way of example only as 0.1 mA. Bracketing begins by stimulating with a current at the midpoint of the initial bracket. If the stimulation current recruits, the bracket shrinks to the lower half of the previous range. If the stimulation current does not recruit, the bracket shrinks to the upper half of the previous range. This process continues until $I_{thresh}$ is bracketed by stimulation currents separated by the selected width or resolution, 0.1 mA in this example. $I_{thresh}$ is preferably defined as the midpoint of this final bracket but any value falling within the bracket may be selected. The bracketing and bisection steps may be repeated for all channels until $I_{thresh}$ is determined for each one.

Significantly, the algorithm further operates to reduce the number of actual stimulations required to complete bracketing and bisection when $I_{thresh}$ is determined repeatedly and/or over multiple channels. The algorithm does so by omitting stimulations for which the result is predictable from data acquired during previous stimulations. When a stimulation is omitted the algorithm proceeds as if the stimulation had taken place. Instead of reporting an actual recruitment result, however, the reported result is inferred from the previous data. This permits the algorithm to proceed to the next step immediately, without the delay associated with a stimulation.

For every stimulation signal delivered, the EMG response, or lack there of, is detected and recorded on each channel, no matter which channel is actually being processed for $I_{thresh}$. That is, every channel either recruits or does not recruit (again, a channel is said to have recruited if a stimulation signal evokes a significant EMG response from the muscle associated with that channel) in response to a given stimulation signal. These recruitment results are detected and saved for each channel. Later, when a different channel is processed for $I_{thresh}$, the saved data can be referred back to such that the algorithm may omit a stimulation if it may infer whether or not the channel would recruit at the given stimulation current.

There are two scenarios in which the algorithm may omit a stimulation and report previously obtained recruitment results. A stimulation may be omitted if the selected stimulation current would be a repeat of a previous stimulation. By way of example only, if a stimulation at 1.0 mA was performed to determine $I_{thresh}$ for one channel, and a stimulation at 1.0 mA is later required to determine $I_{thresh}$ for another channel, the algorithm may omit the stimulation and report the previous results. If the specific stimulation current required has not previously been used, a stimulation may still be omitted if the results are already clear from the previous data. By way of example only, if a stimulation at 2.0 mA was performed to determine $I_{thresh}$ for a previous channel and the present channel did not recruit, when a stimulation at 1.0 mA is later required to determine $I_{thresh}$ for the present channel, the algorithm may infer that the present channel will not recruit at 1.0 mA since it did not recruit at 2.0 mA. The algorithm may omit the stimulation and report the previous result.

Figure 6:
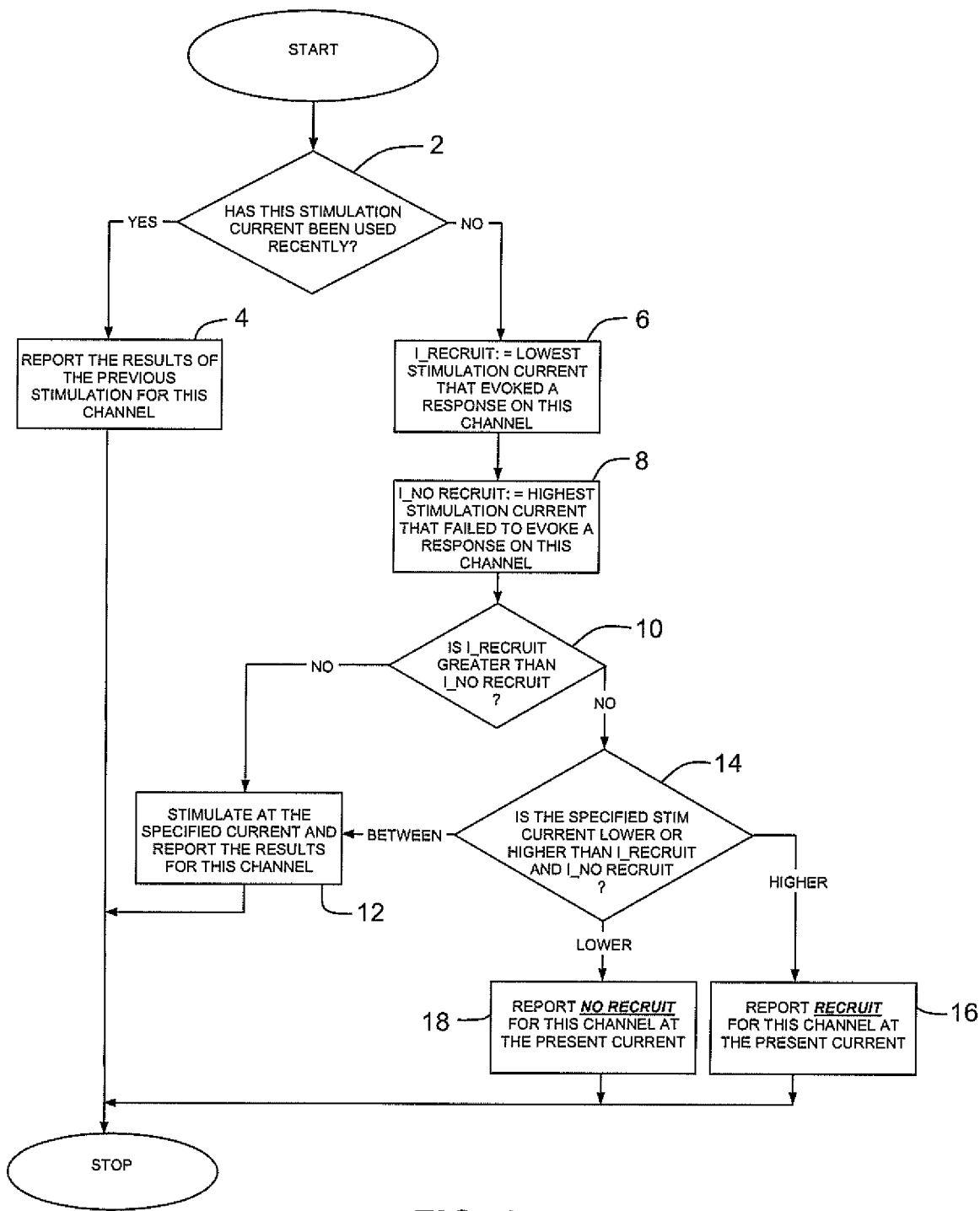
FIG. 6 is a flowchart illustrating the method by which the algorithm determines whether to perform or omit a stimulation.

FIG. 6 illustrates (in flowchart form) a method by which the algorithm determines whether to deliver an actual stimulation or omit the stimulation and report previous results. The algorithm first determines if the selected stimulation current has been previously used (step 2). If the stimulation current has been used the stimulation is omitted and the results of the previous stimulation are reported for the present channel (step 4). If the stimulation current has not been used, the algorithm determines $I_{recruit}$ (step 6) and $I_{norecruit}$ (step 8) for the present channel. $I_{recruit}$ is the lowest stimulation current that has recruited on the present channel. $I_{norecruit}$ is the highest stimulation current that has failed to recruit on the present channel. Next the algorithm ensures $I_{recruit}$ is greater than $I_{norecruit}$ (step 10). An $I_{recruit}$ that is less than or equal to $I_{norecruit}$ is indicative of a changing $I_{thresh}$. Thus, previous results are not likely reflective of the present threshold state and the algorithm will not use them to infer a response to a given stimulation current. The algorithm will stimulate at the selected current and report the results for the present channel (step 12). If $I_{recruit}$ is greater than $I_{norecruit}$ the algorithm next identifies whether the selected stimulation current is higher than $I_{recruit}$, lower than $I_{norecruit}$, or between $I_{recruit}$ and $I_{norecruit}$ (step 14). If the selected stimulation current is higher than $I_{recruit}$ the algorithm omits the stimulation and reports that the present channel recruits at the specified current (step 16). Conversely, when the selected stimulation current is lower than $I_{norecruit}$ the algorithm infers that the present channel will not recruit at the selected current and reports that result (step 18). If the selected stimulation current falls between $I_{recruit}$ and $I_{norecruit}$ the result of the stimulation cannot be inferred. The algorithm stimulates at the selected current and reports the results for the present channel (step 12). This method may be repeated until $I_{thresh}$ has been determined for every active channel.

Figure 7A:
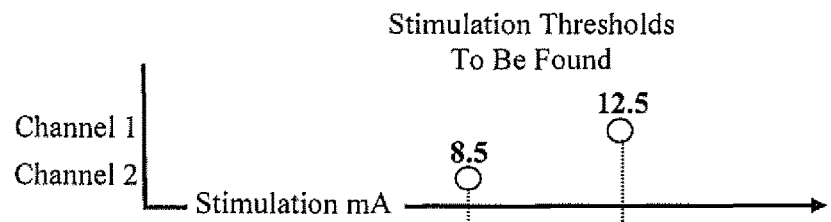
FIGS. 7A-7C are graphs illustrating use of the threshold hunting algorithm of FIG. 5 and further omitting stimulations when the likely result is already clear from previous data.
Figure 7B:
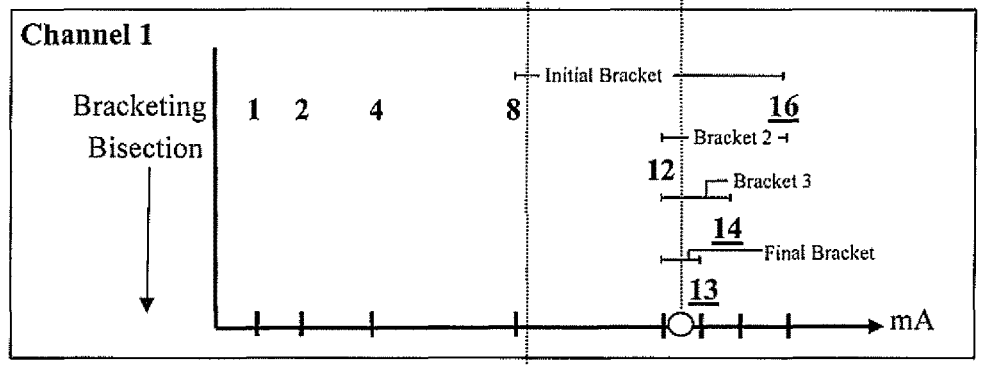
Figure 7C:
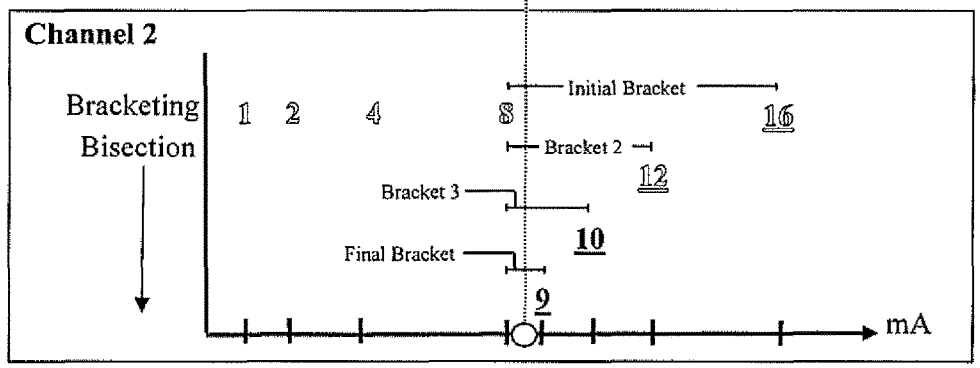

For the purposes of example only, FIGS. 7A-7C demonstrate use of the algorithm of the present invention to determine $I_{thresh}$ on two channels. It should be appreciated, however, that the algorithm of the present invention is not limited to finding $I_{thresh}$ for two channels but may be used to find $I_{thresh}$ for any number of channels. It should also be appreciated that the current levels used herein are for exemplary purposes only and the current levels utilized during an actual implementation may vary considerably from very low currents (e.g. 0.1 mA) to very high currents (e.g. 1000 mA), depending upon a number of factors, including, but not necessarily limited to, the function being performed and individual patient characteristics, among others. With reference to FIG. 7A, channel 1 has an $I_{thresh}$ to be found of 12.5 mA and channel 2 has an $I_{thresh}$ to be found of 8.5 mA. $I_{thresh}$ for channel 1 is found first, using the bracketing and bisection methods discussed above, as illustrated in FIG. 7B. Bracketing begins at the minimum stimulation current (for the purposes of example only) of 1 mA. As this is the first channel processed and no previous recruitment results exist, no stimulations are omitted. The stimulation current is doubled with each successive stimulation (i.e. 1 mA→2 mA→4 mA→8 mA→16 mA) until a significant EMG response is finally evoked at 16 mA. The initial bracket of 8 mA-16 mA is bisected, using the bisection method described above (i.e. 12 mA (midpoint of initial bracket)→14 mA (midpoint of bracket 2)→13 mA (midpoint of bracket 3)), until the stimulation threshold is determined to be 12.5 mA, the midpoint of the final bracket. Having found $I_{thresh}$ on channel 1 the algorithm may turn to channel 2, as illustrated in FIG. 7C. The algorithm begins to process channel 2 by determining the initial bracket, which is again 8 mA-16 mA. In doing so the algorithm refers back to the data obtained for channel 2 during channel 1 processing. All the stimulation currents required in the bracketing state were used in determining $I_{thresh}$ for channel 1. From the data gathered during channel 1 processing the algorithm infers that channel 2 will not recruit at stimulation currents of 1, 2, 4, and 8 mA and will recruit at 16 mA. These stimulations are omitted and the inferred results are reported in turn.

The first stimulation current selected in the bisection state, 12 mA, was used previously and the algorithm may omit the stimulation and report that channel 2 recruits at that stimulation current. The next stimulation current selected in the bisection phase, 10 mA, was not previously used and the algorithm must therefore determine whether the result of a stimulation at 10 mA may still be inferred. $I_{recruit}$ and $I_{norecruit}$ are determined to be 12 mA and 8 mA respectively. 10 mA lies inbetween the $I_{recruit}$ value of 12 mA and $I_{norecruit}$ value of 8 mA, thus the result may not be inferred from the previous data and the stimulation may not be omitted. The algorithm stimulates at 10 mA and reports that the channel recruits. The bracket shrinks to the lower half, making 9 mA the next stimulation current. 9 mA has not previously been used so the algorithm again determines $I_{remit}$ and $I_{norecruit}$, now 10 mA and 8 mA respectively. The selected stimulation current, 9 mA, falls inbetween $I_{recruit}$ and $I_{norecruit}$, thus, the algorithm stimulates at 9 mA and reports the results. The bracket now stands at its final width of 1 mA (for the purposes of example only) and the midpoint of the bracket, 8.5 mA, is selected and reported as $I_{thresh}$ for channel 2.

Although the algorithm is discussed and shown to process channels in numerical order, it will be understood that the actual order in which channels are processed is immaterial. The channel processing order may be biased to yield the highest or lowest threshold first (discussed below) or an arbitrary processing order may be used. Furthermore, it will be understood that it is not necessary to complete the algorithm for one channel before beginning to process the next channel. Channels are still processed one at a time, however, the algorithm may cycle between one or more channels, processing as few as one stimulation current for that channel before moving on to the next channel. By way of example only, the algorithm may stimulate at 1 mA while processing a first channel for $I_{thresh}$. Before stimulating at 2 mA (the next stimulation current in the bracketing phase) the algorithm may cycle to any other channel and process it for the 1 mA stimulation current (omitting the stimulation if applicable). Any or all of the channels may be processed this way before returning to the first channel to apply the next stimulation. Likewise, the algorithm need not return to the first channel to stimulate at 2 mA, but instead, may select a different channel to process first at the 2 mA level. In this manner the algorithm may advance all channels essentially together and bias the order to find the lower threshold channels first or the higher threshold channels first. By way of example only, the algorithm may stimulate at one current level and process each channel in turn at that level before advancing to the next stimulation current level. The algorithm may continue in this pattern until the channel with the lowest $I_{thresh}$ is bracketed. The algorithm may then process that channel exclusively until $I_{thresh}$ is determined, then return to processing the other channels one stimulation current level at a time until the channel with the next lowest $I_{thresh}$ is bracketed. This process may be repeated until $I_{thresh}$ is determined for each channel in order of lowest to highest $I_{thresh}$. Should $I_{thresh}$ for more than one channel fall within the same bracket, the bracket may be bisected, processing each channel within that bracket in turn until it becomes clear which one has the lowest $I_{thresh}$. If it becomes more advantageous to determine the highest $I_{thresh}$ first, the algorithm may continue in the bracketing state until the bracket is found for every channel and then bisect each channel in descending order.

Figure 8:
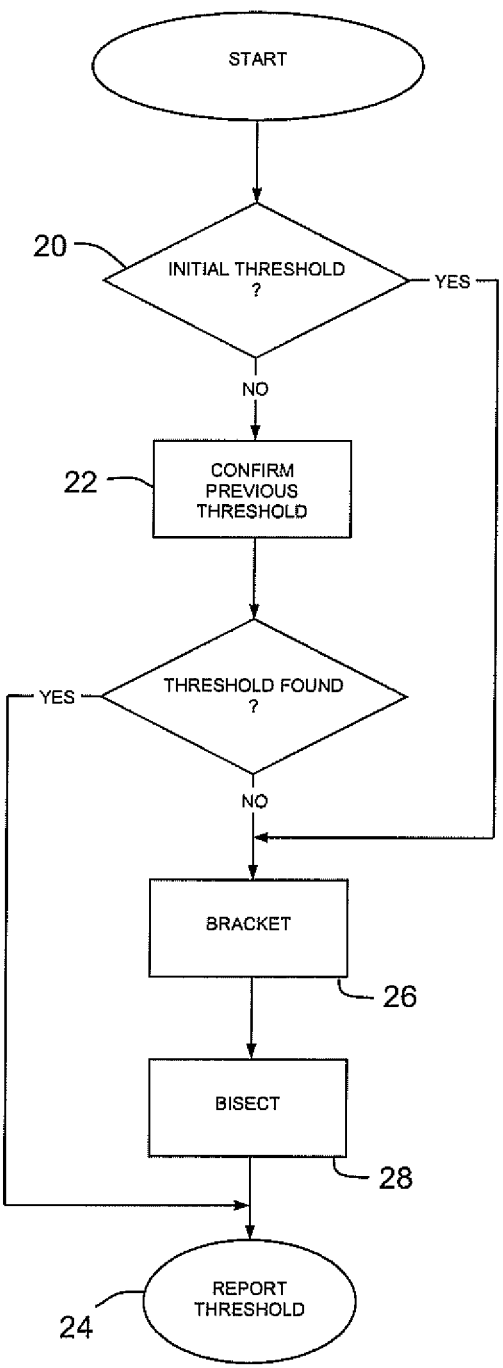
FIG. 8 is a flowchart illustrating the sequence employed by the algorithm to determine and monitor $I_{thresh}$.

In another significant aspect of the present invention, to further reduce the number of stimulations required to repeatedly find $I_{thresh}$ over the course of a procedure, the algorithm includes a confirmation step. If $I_{thresh}$ has been previously determined for a specific channel the algorithm may simply confirm that $I_{thresh}$ has not changed rather than beginning anew with the bracketing and bisection methods. FIG. 8 illustrates the overall sequence the algorithm follows to determine $I_{thresh}$. The algorithm first determines whether it is conducting the initial threshold determination for the channel or whether there is a previous $I_{thresh}$ determination (step 20). If it is not the initial determination the algorithm confirms the previous determination (step 22), as described below. If the previous threshold is confirmed the algorithm reports that value as the present $I_{thresh}$ (step 24). If it is the initial $I_{thresh}$ determination or if the previous threshold cannot be confirmed, the algorithm enters the bracketing (step 26) and bisection (step 28) states to determine $I_{thresh}$ and then reports the value (step 24).

Figure 9:
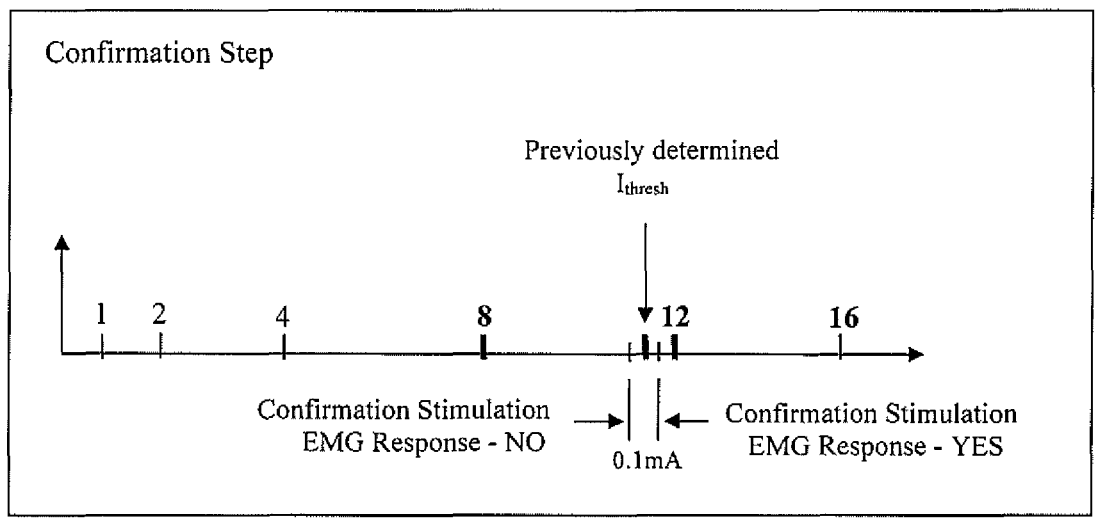
FIG. 9 is a graph illustrating the confirmation step employed by the algorithm to determine whether $I_{thresh}$ has changed from a previous determination.

FIG. 9 illustrates, by way of example only, a method employed by the algorithm for confirming a previous threshold, $I_{thresh}$. The confirmation step attempts to ascertain whether $I_{thresh}$ has moved from its last known value. To do this the algorithm applies two stimulation currents, one at or just above the threshold value and one just below the threshold value. If the stimulation at or above $I_{thresh}$ recruits and the stimulation just below $I_{thresh}$ does not recruit then Ithresh is confirmed and the algorithm may report the initial value again as $I_{thresh}$ and proceed to process another channel. If the stimulation just below $I_{thresh}$ recruits it may be concluded that $I_{thresh}$ has decreased and likewise, if the stimulation at or just above $I_{thresh}$ fails to recruit it may be assumed that $I_{thresh}$ has increased and therefore $I_{thresh}$ can not be confirmed.

If $I_{thresh}$ cannot be confirmed the algorithm enters the bracketing state. Rather than beginning the bracketing state from the minimum stimulation current, however, the bracketing state may begin from the previous $I_{thresh}$. The bracketing may advance up or down depending on whether $I_{thresh}$ has increased or decreased. By way of example only, if the previous value of $I_{thresh}$ was 4 mA the confirmation step may stimulate at 4 mA and 3.8 mA. If the stimulation at 4 mA fails to evoke a significant response it may be concluded that the $I_{thresh}$ has increased and the algorithm will bracket upwards from 4 mA. When the algorithm enters the bracketing state the increment used in the confirmation step (i.e. 0.2 mA in this example) is doubled. Thus the algorithm stimulates at 4.4 mA. If the channel fails to recruit at this current level the increment is doubled again to 0.8 mA, and the algorithm stimulates at 5.2 mA. This process is repeated until the maximum stimulation current is reached or the channel recruits, at which time it may enter the bisection state.

If, during the confirmation step, the stimulation current just below the previously determined $I_{thresh}$ recruits, it may be concluded that $I_{thresh}$ for that channel has decreased and the algorithm may bracket down from that value (i.e. 3.8 mA in this example). Thus, in this example the algorithm would double the increment to 0.4 mA and stimulate at 3.4 mA. If the channel still recruits at this stimulation current the increment is doubled again to 0.8 mA such that the algorithm stimulates at 2.6 mA. This process is repeated until the minimum stimulation current is reached, or the channel fails to recruit, at which time the algorithm may enter the bisection state. The confirmation step may be performed for each channel, in turn, in any order. Again stimulations may be omitted and the algorithm may begin processing a new channel before completing the algorithm for another channel, as described above.

Figure 10:
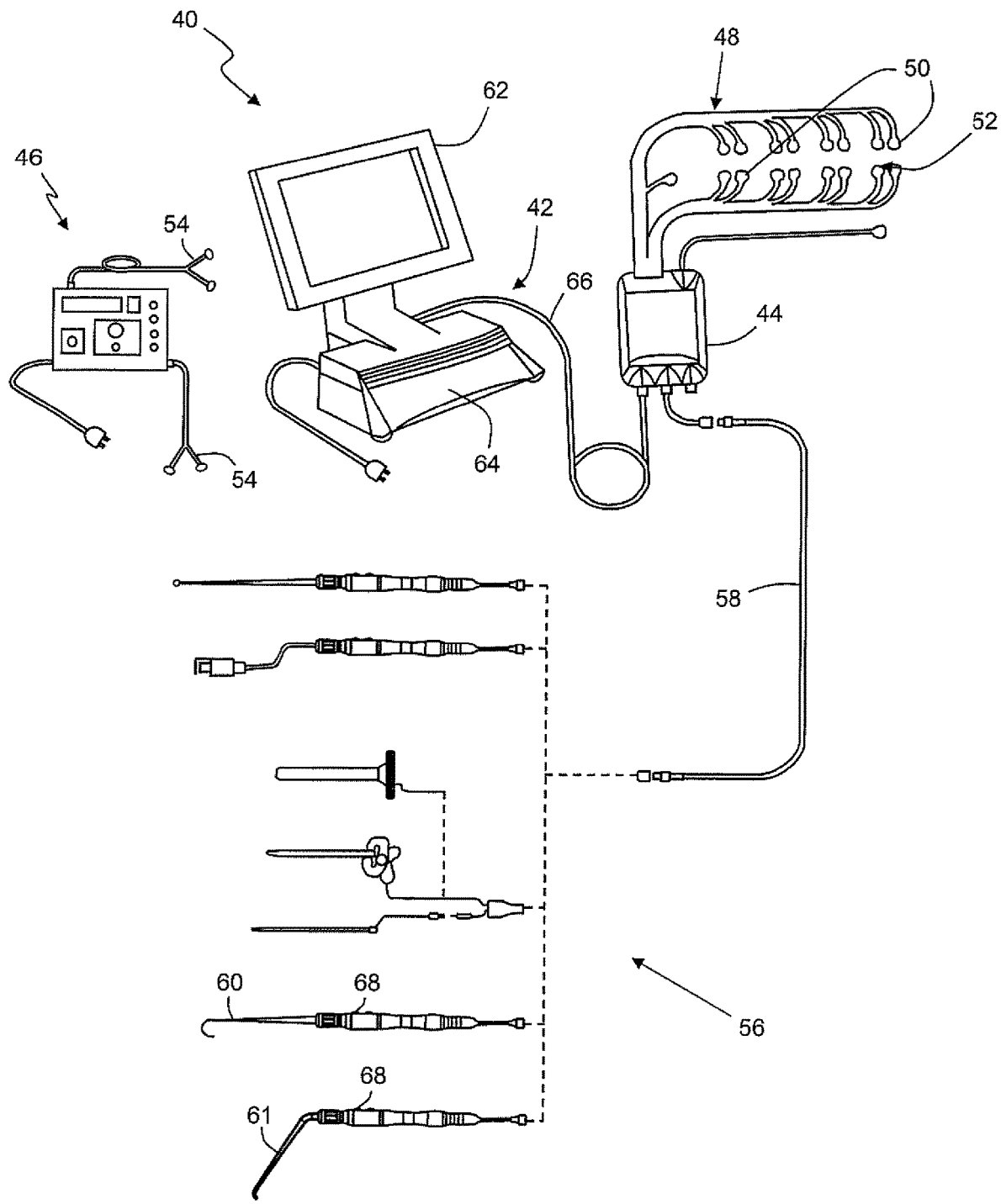
FIG. 10 is a perspective view of an exemplary surgical system 40 capable of employing the algorithm of the present invention to monitor $I_{thresh}$ over a multitude of channels.

By way of example only, the algorithm of the present invention may be particularly useful when employed to monitor nerve pathology in conjunction with the use of a nerve retractor, such as nerve retractor 60 and 61 (shown in FIG. 10). A typical nerve retractor serves to pull or otherwise maintain a nerve outside the surgical corridor, thereby protecting the nerve from inadvertent damage or contact by the "active" instrumentation used to perform the actual surgery. While generally advantageous, it has been observed that such retraction can cause nerve function to become impaired or otherwise pathologic over time due to the retraction. Monitoring $I_{thresh}$ during nerve retraction may be useful to assess the degree to which retraction of a nerve or neural structure affects the nerve function over time. One advantage of such monitoring is that the conduction of the nerve may be monitored during the procedure to determine whether the neurophysiology and/or function of the nerve changes (for the better or worse) as a result of the particular surgical procedure. For example, it may be observed that the nerve conduction decreases (indicated by an increase in $I_{thresh}$ over time) during the retraction, indicating that the nerve function has been negatively affected. In contrast, the nerve conduction may increase (indicated by a decrease in $I_{thresh}$ over time), indicating that the nerve function may have been restored or improved by the surgical procedure (such as during a successful decompression surgery, etc. . . . ). As mentioned, a change in $I_{thresh}$ may occur on any channel; therefore it is advantageous to calculate the actual $I_{thresh}$ for each channel, as opposed to determining a value for just the channel with the highest or lowest $I_{thresh}$. The algorithm of the present invention accomplishes this while substantially limiting the number of stimulations required to do so. This may substantially reduce the time required to make an $I_{thresh}$ determination which in turn may reduce the overall surgical time and risk to the patient.

By way of example only, the algorithm of the present invention may also be of particular use during Motor Evoked Potential (MEP) monitoring. When surgical procedures are performed in the proximity of the spinal cord, potential damage to the spinal cord is a paramount concern. Consequences of spinal cord damage may range from a slight loss of sensation to complete paralysis of the extremities, depending on the location and extent of damage. MEP monitoring, generally involving monitoring transmission of an electrical signal along the spinal cord, may be employed to assess the spinal cord before, during, and/or after surgery. Degradation or decreased conduction of an electrical signal, indicated by an increase in $I_{thresh}$, may indicate that the health of the spinal cord is compromised. Obtaining such information quickly may allow the surgeon to initiate corrective measures before the damage gets worse and/or becomes permanent. Similar to the nerve pathology monitoring mentioned above, changes in $I_{thresh}$ indicating potential damage to the spinal cord may occur on any monitored channel, thus it is advantageous to calculate the actual $I_{thresh}$ for each channel, as opposed to determining just the channel with the highest or lowest $I_{thresh}$. Employing the algorithm of the present invention again allows this to be done accurately and efficiently.

The algorithm of the present invention may be employed for use on any of a number of neurophysiology monitoring systems, including but not limited to that shown and described in commonly owned Int'l Patent App. No. PCT/US02/30617, entitled "System and Methods for Performing Surgical Procedures and Assessments," filed on Sep. 25, 2002; and Intl Patent App. No. PCT/US2006/003966, entitled "System and Methods for Performing Neurophysiologic Assessments During Spine Surgery," filed on Feb. 2, 2006, both of which are hereby incorporated by reference as if set forth fully herein. FIG. 10 illustrates, by way of example only, a multi-channel neurophysiology monitoring system for employing the algorithm of the present invention to quickly find stimulation thresholds for a multitude of channels. By way of example only, the neuromonitoring system 40 may be capable of carrying out neurophysiologic assessment functions including, but not necessarily limited to, Twitch Test (neuromuscular pathway assessment), Screw Test (pedicle integrity testing), Detection (nerve proximity testing during surgical access), Nerve Retractor (nerve pathology monitoring), MEP (Motor Evoked Potential spinal cord monitoring), and SSEP (Somatosensory Evoked Potential spinal cord monitoring). It is expressly noted that, although described herein largely in terms of use in spinal surgery, the neuromonitoring system 10 and related methods of the present invention are suitable for use in any number of additional surgical procedures where neurological impairment is a concern.

The surgical system 40 includes a control unit 42, a patient module 44, an MEP stimulator 46, an EMG harness 48, including eight pairs of EMG electrodes 50 and a return (anode) electrode 52 coupled to the patient module 44, at least one pair of stimulation electrodes 54 coupled to the MEP stimulator 46, and a host of surgical accessories 56 capable of being coupled to the patient module 44 via one or more accessory cables 58. The surgical accessories 56 may include, but are not necessarily limited to, a neural pathology monitoring device such as nerve root retractors 60 and 62. Additional surgical accessories may include stimulation accessories (such as a screw test probe 70 and dynamic stimulation clips 72, 74), surgical access components (such as a K-wire 76, one or more dilating cannula 78, a working cannula 80, and a tissue retraction assembly 82).

Figure 11:
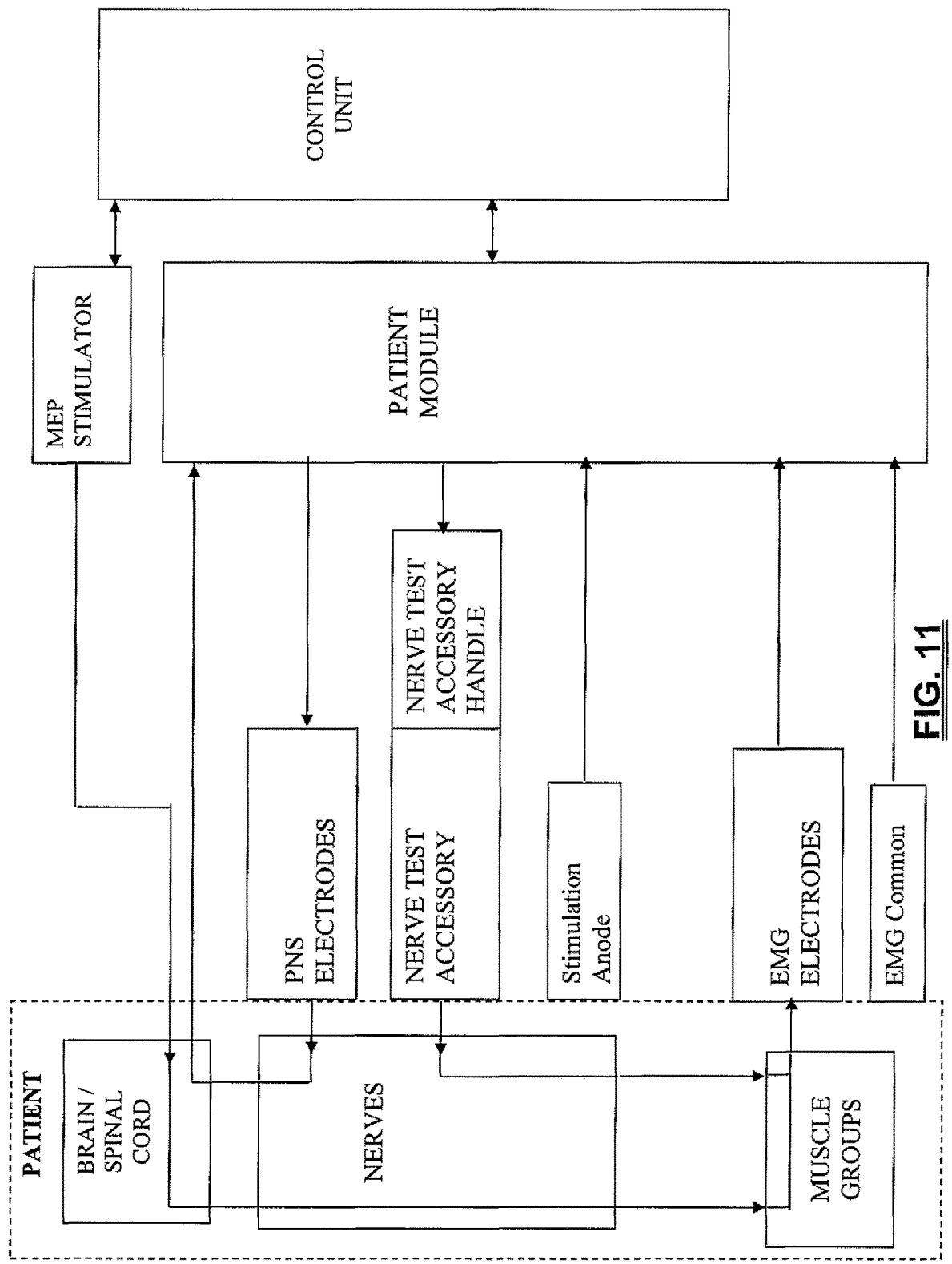
FIG. 11 is a block diagram of the surgical system 40 shown in FIG. 10.

FIG. 11 is a block diagram of the surgical system 40, the operation of which will be explained in conjunction with FIG. 10. The control unit 42 includes a touch screen display 64 and a base 66, which collectively contain the essential processing capabilities for controlling the surgical system 40. The touch screen display 64 is preferably equipped with a graphical user interface (GUI) capable of graphically communicating information to the user and receiving instructions from the user. The base 66 contains computer hardware and software that commands the stimulation sources (e.g. MEP stimulator 46 and patient module 44) receives digital and/or analog signals and other information from the patient module 44, processes the EMG responses, and displays the processed data to the operator via the display 64. The primary functions of the software within the control unit 42 include receiving user commands via the touch screen display 64, activating stimulation in a requested mode, Detection, and Nerve Retractor), processing signal data according to defined algorithms (described below), displaying received parameters and processed data, and monitoring system status.

The patient module 44 is connected via a data cable 67 to the control unit 42, and contains the electrical connections to electrodes, signal conditioning circuitry, stimulator drive and steering circuitry, and a digital communications interface to the control unit 42. In use, the control unit 42 is situated outside but close to the surgical field (such as on a cart adjacent the operating table) such that the display 64 is directed towards the surgeon for easy visualization. The patient module 44 may be located near the patient's legs or may be affixed to the end of the operating table at mid-leg level using a bedrail clamp. The position selected should be such that all EMG electrodes can reach their farthest desired location without tension during the surgical procedure. The information displayed to the user on the display 62 may include, but is not necessarily limited to, alpha-numeric and/or graphical information regarding MEP, nerve pathology, myotome/EMG levels, stimulation levels, the function selected, and the instrument in use.

In a preferred embodiment, EMG response monitoring for the system 40 is accomplished via 8 pairs of EMG electrodes 50 placed on the skin over the muscle groups to be monitored, a common electrode 51 providing a ground reference to pre-amplifiers in the patient module 44, and an anode electrode 52 providing a return path for the stimulation current. The EMG responses provide a quantitative measure of the nerve depolarization caused by the electrical stimulus. It should be appreciated that any of a variety of known electrodes can be employed with system 40, including but not limited to surface pad electrodes and needle electrodes. A preferred EMG electrode is the dual surface electrode which is shown and described in detail in the commonly owned and co-pending U.S. patent application Ser. No. 11/048,404, entitled "Improved Electrode System and Related Methods," filed on Jan. 31, 2005, which is expressly incorporated by reference into this disclosure as if set forth in its entirety herein.

The arrangement of EMG electrodes depends on a multitude of factors, including for example, the spinal cord level, neural tissue at risk, and user preference, among others. In one embodiment (set forth by way of example only), the preferred EMG configuration is described for Lumbar surgery in Table 1, Thoracolumbar surgery in Table 2, and Cervical surgery in Table 3 below:

TABLE 1

Lumbar

| Color | Channel | Myotome | Nerve | Spinal Level |
|---|---|---|---|---|
| Red | Right 1 | Right Vastus Medialis | Femoral | L2, L3, L4 |
| Orange | Right 2 | Right Tibialis Anterior | Common Peroneal | L4, L5 |
| Yellow | Right 3 | Right Biceps Femoris | Sciatic | L5, S1, S2 |
| Green | Right 4 | Right Medial Gastroc. | Post Tibial | S1, S2 |
| Blue | Left 1 | Left Vastus Medialis | Femoral | L2, L3, L4 |
| Violet | Left 2 | Left Tibialis Anterior | Common Peroneal | L4, L5 |
| Gray | Left 3 | Left Biceps Femoris | Sciatic | L5, S1, S2 |
| White | Left 4 | Left Medial Gastroc. | Post Tibial | S1, S2 |

TABLE 2

Thoracolumbar

| Color | Channel | Myotome | Nerve | Spinal Level |
|---|---|---|---|---|
| Red | Right 1 | Right Abductor Pollicis Brevis | Median | C6, C7, C8, T1 |
| Orange | Right 2 | Right Vastus Medialis | Femoral | L2, L3, L4 |
| Yellow | Right 3 | Right Tibialis Anterior | Common Peroneal | L4, L5 |
| Green | Right 4 | Right Abductor Hallucis | Tibial | L4, L5, S1 |
| Blue | Left 1 | Left Abductor Pollicis Brevis | Median | C6, C7, C8, T1 |
| Violet | Left 2 | Left Vastus Medialis | Femoral | L2, L3, L4 |
| Gray | Left 3 | Left Tibialis Anterior | Common Peroneal | L4, L5 |
| White | Left 4 | Left Abductor Hallucis | Tibial | L4, L5, S1 |

TABLE 3

Cervical

| Color | Channel | Myotome | Nerve | Spinal Level |
|---|---|---|---|---|
| Red | Right 1 | Right Deltoid | Axilliary | C5, C6 |
| Orange | Right 2 | Right Flexor Carpi Radialis | Median | C6, C7, C8 |
| Yellow | Right 3 | Right Abductor Pollicis Brevis | Median | C6, C7, C8, T1 |
| Green | Right 4 | Right Abductor Hallucis | Tibial | L4, L5, S1 |
| Blue | Left 1 | Left Deltoid | Axilliary | C5, C6 |
| Violet | Left 2 | Left Flexor Carpi Radialis | Median | C6, C7, C8 |
| Gray | Left 3 | Left Abductor Pollicis Brevis | Median | C6, C7, C8, T1 |
| White | Left 4 | Left Abductor Hallucis | Tibial | L4, L5, S1 |

The surgical system 40 employs the algorithm described above to automatically control the delivery of stimulation signals upon test initiation. While it may be used with any of a number of the operable functions of system 40, the multi-channel aspect of the hunting algorithm is most particularly useful during Nerve Retractor and MEP modes, which will be described in greater detail below. Various additional functions of the system 40 have been previously discussed in detail elsewhere and such discussion is not included herein. Details of the Twitch Test, Screw Test (Basic, Difference, Dynamic), Detection, and SSEP modes may be found in the following commonly owned patent applications, each of which is expressly incorporated by reference as if set forth herein in their entireties: Int'l Patent App. No. PCT/US2005/036089, entitled "System and Methods for Assessing the Neuromuscular Pathway Prior to Nerve Testing," filed Oct. 7, 2005; Int'l Patent App. No. PCT/US02/35047 entitled "System and Methods for Performing Percutaneous Pedicle Integrity Assessments," filed on Oct. 30, 2002; Int'l Patent App. No. PCT/US2004/025550, entitled "System and Methods for Performing Dynamic Pedicle Integrity Assessments," filed on Aug. 5, 2004; Int'l Patent App. No PCT/US02/22247, entitled "System and Methods for Determining Nerve Proximity, Direction, and Pathology During Surgery," filed on Jul. 11, 2002; the entire contents of each are hereby incorporated by reference as if set forth fully herein.

The surgical system 40 accomplishes neural pathology monitoring (via Nerve Retractor Mode, by way of example only) by electrically stimulating a nerve root according to the hunting algorithm, via one or more stimulation electrodes at the distal end of the nerve root retractor 60 or 61 and monitoring each channel for corresponding evoked muscle responses. Threshold hunting continues according to the algorithm until $I_{thresh}$ is determined for each channel in range. A pathology assessment is made by determining a baseline stimulation threshold with direct contact between the nerve retractor 60 or 61 and the nerve, prior to retraction. Subsequent stimulation thresholds are determined during retraction and they are compared to the baseline threshold. An increase in $I_{thresh}$ over time is an indication that the nerve function is deteriorating and retraction should be reduced or stopped altogether to prevent permanent damage. A decrease in $I_{thresh}$ over time may be an indication that nerve function has been at least partially restored.

Figure 12:
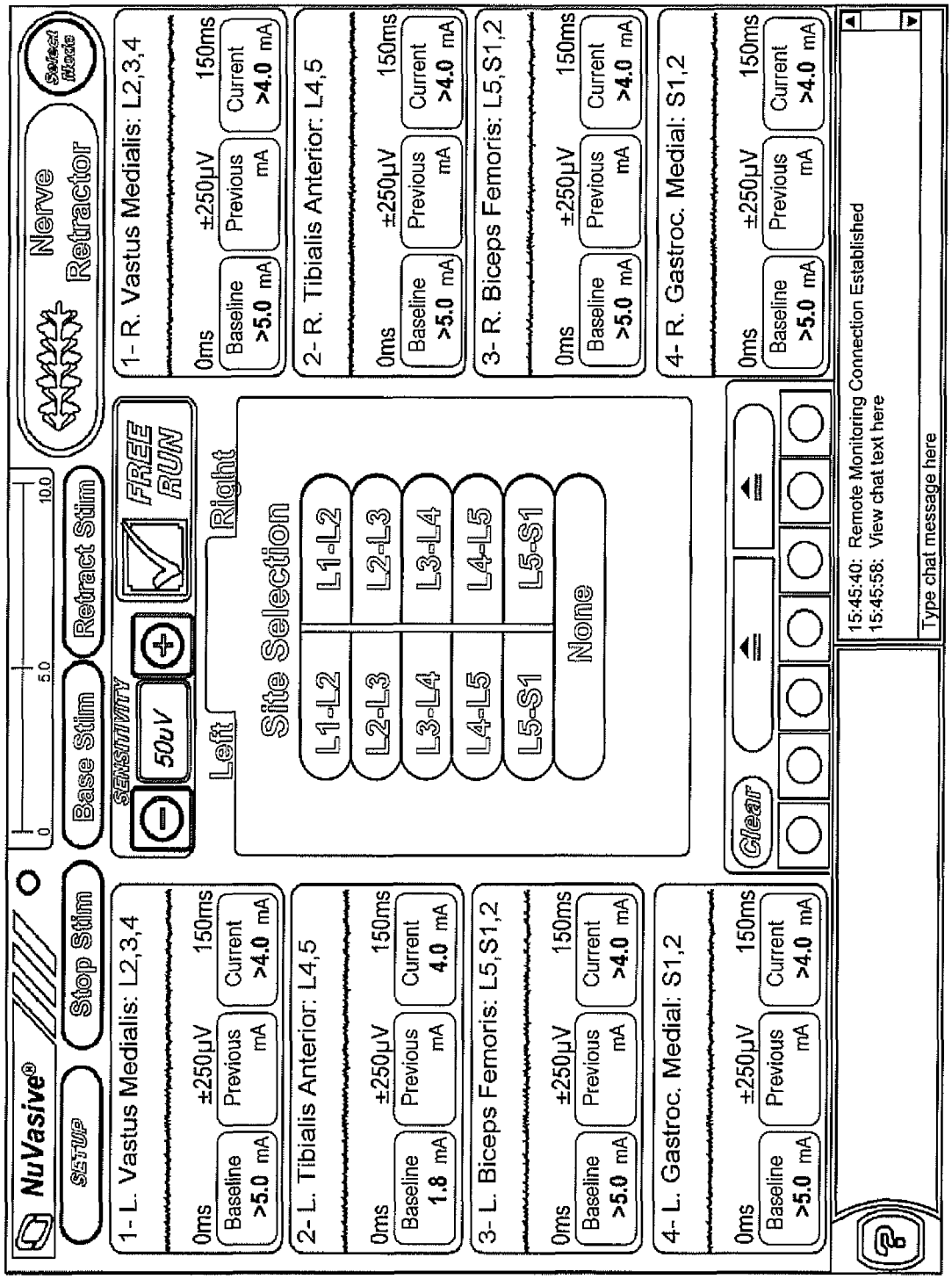
FIG. 12 is an exemplary screen display illustrating one embodiment of a nerve pathology monitoring function of the surgical system 40 utilizing the algorithm of the present invention to determine $I_{thresh}$.

$I_{thresh}$ results determined by the algorithm may be displayed to the surgeon on the display 62, as illustrated, by way of example only, in FIG. 12. Preferably, baseline, directly previous, and current Ithresh results are shown for each channel. The display of $I_{thresh}$ values may be accompanied by a color code making use of the colors Red, Yellow, and Green. The color Red may be displayed when the difference between the baseline and actual value is within a predetermined "unsafe" level. The color green may be displayed when the difference between the baseline $I_{thresh}$ and current $I_{thresh}$ is within a predetermined "safe" level. Yellow may be displayed when difference between the baseline $I_{thresh}$ and current $I_{thresh}$ falls between predetermined unsafe and safe levels.

The nerve root retractor 60 may be dimensioned in any number of different fashions, such as retractors 60 and 61 illustrated in FIG. 10, including having a generally curved distal region (shown as a side view in FIG. 10 to illustrate the concave region where the nerve will be positioned while retracted), and of sufficient dimension (width and/or length) and rigidity to maintain the retracted nerve in a desired position during surgery. The nerve root retractors 60, 61 may also be equipped with a handle 68 having one or more buttons for selectively initiating the algorithm and applying the electrical stimulation to the stimulation electrode(s) at the distal end of the nerve root retractor 60, 61. In one embodiment, the nerve root retractor 60, 61 is disposable and the handle 68 is reusable and autoclavable.

The surgical system 40 may perform MEP by electrically stimulating the motor cortex of the brain with electrical stimulation signals which creates an action potential that travels along the spinal cord and into the descending nerves, evoking activity from muscles innervated by the nerves. EMG responses of the muscles are recorded by the system 40 and analyzed in relation to the stimulation signal. Stimulation and analysis are preferably executed according to the multi-channel hunting algorithm described above.

MEP stimulation signals are generated in the MEP stimulator 21 and delivered to the motor cortex via a pair of stimulation electrodes 54 connected to the MEP stimulator 21 and placed on opposite sides of the cranium. Each MEP signal is preferably delivered as a group or train of multiple pulses, such as that illustrated in FIG. 2. Stimulation signals are delivered at a constant current but MEP stimulator 46 is capable of delivering stimulation signals over a large range of currents in order to execute the hunting algorithm. By way of example only, MEP stimulator 46 may deliver a first stimulation signal at a constant current of 100 mA, a second stimulation signal at constant current of 200 mA, a third stimulation signal of 400 mA, and a fourth stimulation signal of 800 mA. Preferably, stimulation signals may be delivered at a current ranging from 0 mA to 1000 mA. It should be understood of course that the hunting algorithm employed by the system 40 need not be limited to any range. MEP stimulator 46 may deliver either a positive pulse or a negative pulse. Additionally, MEP stimulator 46 may have more than one stimulation channel, thus, additional pairs of stimulation electrodes 54 may be arranged on the skull. This is advantageous in that the effectiveness of a stimulation signal originating from one position on the skull may vary between different recording sites.

MEP stimulator 46 is communicatively linked to the control unit 42 which commands the stimulator 46 to deliver electrical signals according to predetermined parameters (such as current level, among others) at the proper time. MEP stimulator 46 may be communicatively linked to the control unit 40 via any suitable connection such as a data cable or wireless technology, etc. . . . . The MEP stimulator 46 may be positioned outside the sterile area but should be located such that the stimulation electrodes 54, attached to the stimulator 46, may be positioned on the patient's head without tension. By way of example, MEP stimulator 46 may be placed on the surgical table adjacent to the patient's head. Optionally, the MEP stimulator 46 may be fashioned with a mount or hook (not shown) and hung from an IV pole near the patient's head.

The multi-channel threshold hunting algorithm described above is utilized to determine a baseline $I_{thresh}$ for each channel, preferably prior to or in the early stages of a surgical procedure. It should be appreciated, however, that a new baseline $I_{thresh}$ may be determined at any time during the procedure at the option of the surgeon or other qualified operator. Having determined a baseline $I_{thresh}$ for each channel, subsequent monitoring may be performed as desired throughout the procedure and recovery period to obtain updated $I_{thresh}$ values for each channel. Each new determination of $I_{thresh}$ is compared by the surgical system 40 to the baseline $I_{thresh}$ for the appropriate channel. The difference ($\Delta I_{thresh}$) between the baseline $I_{thresh}$ and the new $I_{thresh}$ is calculated by the system 40 and the $\Delta I_{thresh}$ value is compared to predetermined "safe" and "unsafe" values. If $\Delta I_{thresh}$ S greater than the predetermined safe level, the user is alerted to a potential complication and action may be taken to avoid or mitigate the problem. The speed with which the multi-channel MEP threshold hunting algorithm is able to determine $I_{thresh}$ across all channels, and the simplicity with which the data communicated to the user may be interpreted, allows the user to increase the frequency of MEP monitoring conducted during a procedure without a concurrent increase in overall surgery time. This provides significant benefit to the patient by reducing the time intervals in between MEP monitoring episodes during which an injury to the spinal cord may go undetected.

Figure 13:
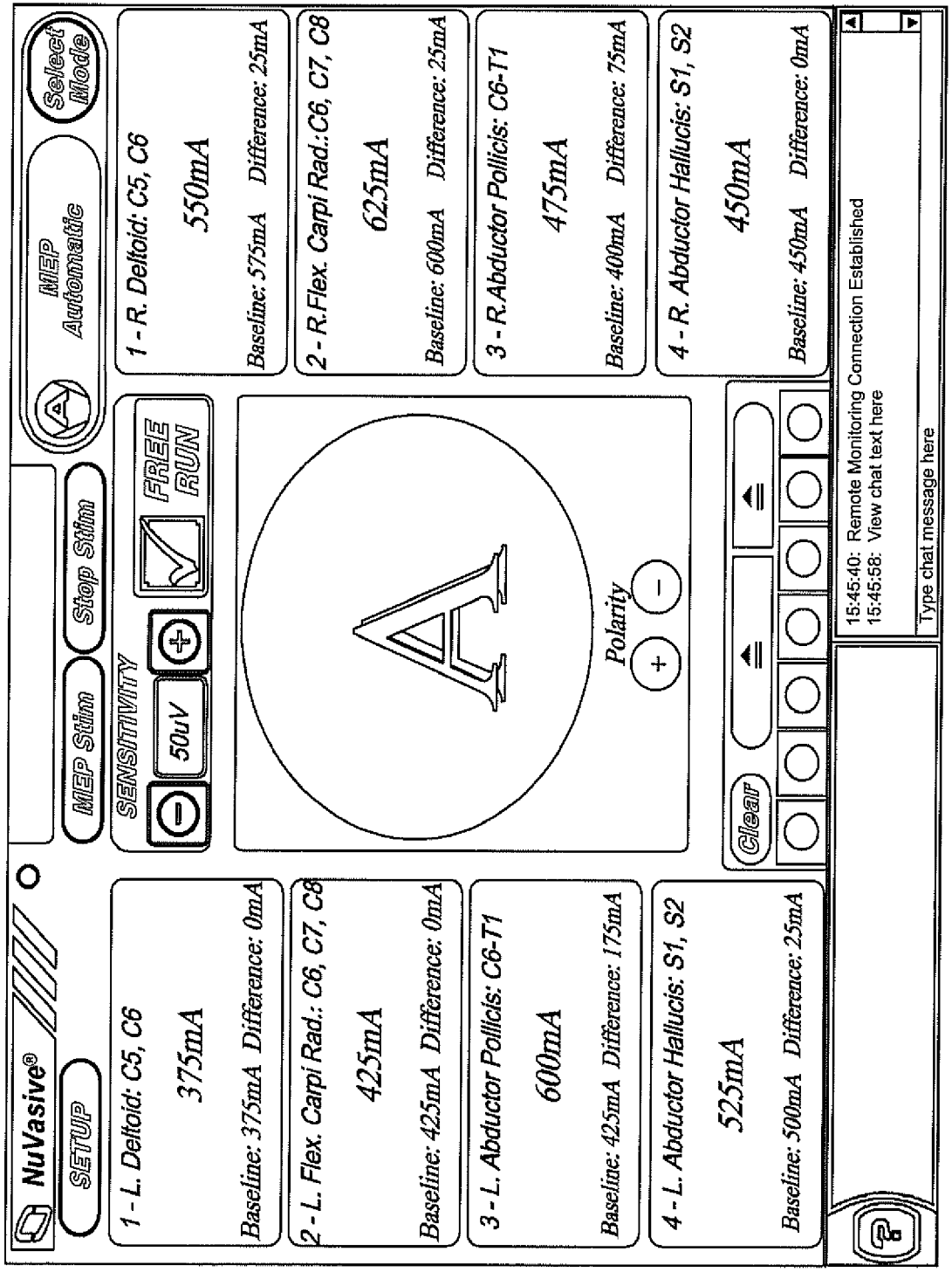
FIG. 13 is an exemplary screen display illustrating one embodiment of a transcranial motor evoked potential monitoring function of the surgical system 40 utilizing the algorithm of the present invention to determine $I_{thresh}$.

The display of $I_{thresh}$, shown by way of example only in the exemplary MEP screen display of FIG. 13, may be accompanied by a color code so that the operator may quickly easily comprehend the situation and avoid neurological impairment to the patient (e.g. red for "danger," yellow for "caution" and green for "safe"). The color Red may be displayed when the difference between the baseline and actual value, $\Delta I_{thresh}$, is within a predetermined "unsafe" level. The color green may be displayed when the $\Delta I_{thresh}$ is within a predetermined "safe" level. Yellow may be displayed when the $\Delta I_{thresh}$ value falls between predetermined unsafe and safe levels.

It will be readily appreciated that various modifications may be undertaken, or certain steps or algorithms omitted or substituted, without departing from the scope of the present invention. By way of example only, although the multi-channel hunting algorithm is discussed herein in terms of finding $I_{thresh}$ (the lowest stimulation current that evokes a significant EMG response), it is contemplated that alternative stimulation thresholds may be determined by the hunting algorithm. By way of example only, the hunting algorithm may be employed to determine a stimulation voltage threshold, $Vstim_{thresh}$. This is the lowest stimulation voltage (as opposed to the lowest stimulation current) necessary to evoke a significant EMG response, $V_{thresh}$. The bracketing and bisection states are conducted, omitting stimulations and conducting confirmation step when applicable, as described above, with brackets based on voltage being substituted for the current based brackets previously described. By way of further example, although use of the multi-channel hunting algorithm was described with reference to a nerve retractor and Tce-MEP monitoring, it will be appreciated that the algorithm may be employed for a variety or neurophysiology functions including, but not necessarily limited to, pedicle integrity testing, nerve proximity monitoring, and nerve direction monitoring.

Moreover, although use of the algorithm was illustrated with reference to the surgical system 40, it will be appreciated as within the scope of the invention to use the multi-channel hunting algorithm as described herein with any number of different neurophysiology based testing, including but not limited to the "NIM SPINE" testing system offered by Medtronic Sofamor Danek, Inc.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A neuromonitoring system for performing multi-channel neurophysiologic assessments, comprising:
    a stimulator configured to deliver at least one electrical stimulation signal to a patient;
    at least one sensor adapted to be coupled to a myotome, said at least one sensor configured to detect a neuromuscular response evoked by said at least one electrical stimulation signal; and
    a control unit in communication with said stimulator and said at least one sensor, said control unit being configured to:
        determine a threshold current level on a first channel of the neuromonitoring system based on a delivery of said at least one electrical stimulation signal, via the stimulator, and an analysis of neuromuscular responses on said first channel, via the at least one sensor, to determine when the at least one electrical stimulation signal evokes a significant neuromuscular response, wherein the threshold current level is a stimulation current level at which a nerve tissue depolarizes, said first channel associated with a first myotome, wherein the significant neuromuscular response comprises a peak-to-peak voltage that is greater than a threshold voltage corresponding to the threshold current level, wherein said at least one electrical stimulation signal are delivered as a sequence of pulses and wherein a current level of each pulse is adjusted from an immediately preceding pulse until the threshold current level required to evoke the significant neuromuscular response is determined; and
        omit one or more pulses from the sequence of pulses when the neuromuscular response to an omitted pulse is predictable based upon data obtained, at the control unit, during determination of the threshold current level of the first channel, wherein the data obtained comprises one or more stimulation current levels corresponding to the delivery of at least one electrical stimulation signal.

2. The system of claim 1, wherein the control unit being configured to determine the threshold current level for the first channel includes the control unit being further configured to:
    establish a bracket within which the threshold current level must lie.

3. The system of claim 1, wherein the control unit being configured to determine the threshold current level for the first channel includes the control unit being further configured to:
    bisect to a predetermined range a bracket established on the first channel.

4. The system of claim 1, wherein the control unit being configured to determine the threshold current level includes the control unit being further configured to:
    assign a specific status to each pulse, said status being one of a first status and a second status, said first status applying to a first current level which evokes a first neuromuscular response one of equal to and greater than a predetermined magnitude and said second status applying to a second current level which evokes a second neuromuscular response less than said predetermined magnitude.

5. The system of claim 4, wherein the control unit being configured to assign the specific status to each pulse includes the control unit being configured to:
    stimulate at a given current level and measure a magnitude of a corresponding neuromuscular response; or
    infer the first status or the second status based on the obtained data.

6. The system of claim 5, wherein said first status is assigned without directing a pulse at said given current level if said given current level is one of equal to and greater than a previous current level assigned to said first status on the first channel.

7. The system of claim 5, wherein said second status is assigned without directing a pulse of the sequence of pulses at said given current level if said given current level is less than a previous current level assigned to said second status on the first channel.

8. The system of claim 5, wherein the control unit being configured to determine the threshold current level includes the control unit being further configured to:
    perform a first step of establishing a bracket within which the threshold current level must lie and a second step of bisecting the bracket to a predetermined width.

9. The system of claim 5, wherein a first bracket is determined by assigning one of said first status and said second status to a series of pulses of the sequence of pulses of successively doubling stimulation current levels, wherein an upper boundary of said first bracket comprises a first stimulation current level assigned said first status and a lower boundary of said first bracket comprises a last stimulation current level assigned said second status.

10. The system of claim 9, wherein said first bracket is bisected by assigning one of said first status and said second status to a stimulation current level at the midpoint of said first bracket, said midpoint forming a second bracket with one of said upper boundary and said lower boundary of said first bracket, said midpoint forming a lower boundary of said second bracket when said midpoint is assigned said second status and said midpoint forming an upper boundary of said second bracket when said midpoint is assigned said first status.

11. The system of claim 1, further comprising:
a display linked to said control unit, wherein the display is configured to display at least one of alpha-numeric, graphic, and color based indicia to communicate results of the threshold current level.

12. The system of claim 11, wherein said display includes a graphical user interface, wherein the graphical user interface is configured to:
receive user instructions including one or more of starting stimulation, stopping stimulation, selecting a function, and adjusting system parameters.

13. The system of claim 1, wherein the control unit being configured to deliver the at least one electrical stimulation signal within tissue includes the control unit being further configured to:
deliver the at least one electrical stimulation signal to a motor cortex via the motor evoked potential stimulator.

14. The system of claim 13, wherein the control unit is further configured to:
compare a later threshold current level to an earlier threshold current level to indicate a health of a spinal cord.

15. The system of claim 1, wherein said significant neuromuscular response is an electromyography response.

16. The system of claim 15, wherein the control unit is further configured to:
assign a specific status to each pulse, said status being one of a first status and a second status, said first status applying to a first current level which evokes a first electromyography response equal to or greater than a predetermined magnitude and said second status applying to a second current level which evokes a second electromyography response less than said predetermined magnitude.

17. The system of claim 16, wherein the control unit being configured to assign the specific status to each pulse includes the control unit being further configured to:
stimulate at a given current level; and
measure a magnitude of a corresponding electromyography response.

18. The system of claim 16, wherein the control unit being configured to assign the specific status to each pulse includes the control unit being further configured to infer the first status or the second status based on previously obtained data.

19. A method of performing multi-channel neurophysiologic assessments using a sequence of pulses delivered to a patient, the method comprising:
determining a threshold current level that causes nerve tissue to depolarize by analyzing one or more neuromuscular responses to a delivered pulse of the sequence of pulses;
determining whether the delivered pulse evokes a significant neuromuscular response that has a peak-to-peak voltage that is greater than a threshold voltage corresponding to the threshold current level;
responsive to the delivered pulse failing to evoke the significant neuromuscular response, adjusting a current level of a next pulse of the sequence of pulses;
determining whether a next neuromuscular response to the next pulse having the adjusted current level is predictable based on data obtained during the determining of the threshold current level, wherein the data obtained comprises one or more stimulation current levels corresponding to delivery of at least one electrical stimulation signal; and
responsive to determining that the next neuromuscular response to the next pulse is predictable, omitting the next pulse from the sequence of pulses.

* * * * *